(12) United States Patent
Millican, Jr. et al.

(10) Patent No.: US 9,718,884 B2
(45) Date of Patent: Aug. 1, 2017

(54) ANTI-TNF-/ANTI-IL-23 BISPECIFIC ANTIBODIES

(71) Applicant: Eli Lilly and Company, Indianapolis, IN (US)

(72) Inventors: Rohn L Millican, Jr., Indianapolis, IN (US); Neungseon Seo, Carmel, IN (US); Songqing Na, San Marcos, CA (US); Catherine B. Beidler, Poway, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/930,678

(22) Filed: Nov. 3, 2015

(65) Prior Publication Data
US 2016/0122429 A1    May 5, 2016

Related U.S. Application Data

(60) Provisional application No. 62/075,571, filed on Nov. 5, 2014.

(51) Int. Cl.
| | |
|---|---|
| C07K 16/24 | (2006.01) |
| A61K 39/395 | (2006.01) |
| C12N 15/13 | (2006.01) |
| C07K 16/28 | (2006.01) |
| A61K 39/00 | (2006.01) |

(52) U.S. Cl.
CPC .......... C07K 16/244 (2013.01); C07K 16/241 (2013.01); C07K 16/2878 (2013.01); A61K 2039/505 (2013.01); A61K 2039/507 (2013.01); A61K 2039/54 (2013.01); A61K 2039/545 (2013.01); C07K 2317/31 (2013.01); C07K 2317/33 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 6,090,382 A | 7/2000 | Salfeld et al. | |
| 7,491,391 B2 | 2/2009 | Benson et al. | |
| 7,510,709 B2 | 3/2009 | Gurney | |
| 7,612,181 B2 | 11/2009 | Wu et al. | |
| 7,872,102 B2 | 1/2011 | Beidler et al. | |
| 7,893,215 B2 | 2/2011 | Bowman et al. | |
| 8,034,341 B2 | 10/2011 | Oft et al. | |
| 8,062,634 B2 | 11/2011 | Bowman et al. | |
| 8,258,268 B2 | 9/2012 | Wu et al. | |
| 8,263,748 B2 | 9/2012 | Li et al. | |
| 8,574,579 B2 | 11/2013 | Benson et al. | |
| 8,722,859 B2 | 5/2014 | Miller et al. | |
| 9,127,057 B2 | 9/2015 | Clarke et al. | |
| 2010/0111966 A1 | 5/2010 | Presta et al. | |
| 2010/0135998 A1 | 6/2010 | Bowman et al. | |
| 2011/0002928 A1 | 1/2011 | Cua et al. | |
| 2011/0110852 A1 | 5/2011 | Miller et al. | |
| 2011/0212104 A1 | 9/2011 | Beaumont et al. | |
| 2012/0251541 A1 | 10/2012 | Baurin et al. | |
| 2013/0280256 A1 | 10/2013 | Allan et al. | |
| 2013/0287775 A1 | 10/2013 | Bowman et al. | |
| 2013/0309194 A1 | 11/2013 | Gurney | |
| 2013/0345404 A1 | 12/2013 | Baurin et al. | |
| 2014/0056895 A1 | 2/2014 | Baurin et al. | |
| 2014/0079705 A1 | 3/2014 | Hsieh et al. | |
| 2014/0255406 A1 | 9/2014 | Allan et al. | |

FOREIGN PATENT DOCUMENTS

| | | |
|---|---|---|
| EP | 2108660 A1 | 10/2009 |
| EP | 2425838 A2 | 3/2012 |
| EP | 1896073 B1 | 3/2013 |
| EP | 1896073 B1 | 6/2013 |
| WO | 9509917 A1 | 4/1995 |
| WO | 0056772 A1 | 9/2000 |
| WO | 2005052157 A1 | 9/2005 |
| WO | 2007024846 A2 | 3/2007 |
| WO | 2007027714 A2 | 3/2007 |
| WO | 2007076524 A2 | 7/2007 |
| WO | 2007005955 A2 | 11/2007 |
| WO | 2007147019 A2 | 12/2007 |
| WO | 2008024188 A2 | 2/2008 |
| WO | 2008103432 A1 | 8/2008 |
| WO | 2008106131 A2 | 9/2008 |
| WO | 2009120922 A2 | 10/2009 |
| WO | 2009149189 A2 | 12/2009 |

(Continued)

OTHER PUBLICATIONS

Wu et al., Syk mediates IL-17-induced CCL20 expression by targeting Act1-dependent K63-linked ubiquitination of TRAF6., J. of Investigative Dermatology (Sep. 2014), 135(2), 490-498.
Fischer, JA. et al. Combined inhibition of TNFα and IL-17 as therapeutic opportunity for treatment in rheumatoid arthritis: development and characterization of a novel bispecific antibody. Arthritis Rheumatol. Jan. 2015;67(1):51-62. doi: 10.1002/art.38896.
Oppmann, Birgit et al. Novel p19 Protein Engages IL-12p40 to Form a Cytokine, IL-23, with Biological Activities Similar as Well as Distinct from IL-12. Immunity. 2000; vol. 13; pp. 715-725.

(Continued)

Primary Examiner — David Romeo
(74) Attorney, Agent, or Firm — Duane C. Marks

(57) ABSTRACT

Bispecific antibodies are provided that bind Tumor Necrosis Factor alpha (TNFα) and the p19 subunit of Interleukin-23 (IL-23p19) and are characterized as having high affinity and strong simultaneous neutralizing properties to both TNFα and IL-23. The bispecific antibodies of the invention are useful for treating various autoimmune diseases including Inflammatory Bowel Disease, such as Crohn's Disease and Ulcerative Colitis, Axial Spondyloarthropathy, Rheumatoid Arthritis and Psoriatic Arthritis.

9 Claims, No Drawings

(56) References Cited

FOREIGN PATENT DOCUMENTS

| WO | 2010121140 A1 | 11/2010 |
|----|---------------|---------|
| WO | 2011070339 A1 | 6/2011  |
| WO | 2012135345 A1 | 10/2012 |
| WO | 2013063110 A1 | 5/2013  |
| WO | 2014100312 A1 | 6/2014  |
| WO | 2014137961 A1 | 9/2014  |
| WO | 2014143540 A1 | 9/2014  |

OTHER PUBLICATIONS

Aggarwal, Sudeepta et al. Interleukin-23 Promotes a Distinct CD4 T Cell Activation State Characterized by the Production of Interleukin-17. The Journal of Biological Chemistry. Jan. 2003; vol. 278; No. 3; pp. 1910-1914.

Langowski, John L. et al. IL-23 promotes tumour incidence and growth. Nature Letters. Jul. 27, 2006; vol. 442; pp. 461-465.

Kikly, Kristine et al. The IL-23/Th17 axis: Therapeutic targets for autoimmune inflammation. Current Opinion in Immunology. 2006; vol. 18; pp. 670-675.

ANTI-TNF-/ANTI-IL-23 BISPECIFIC ANTIBODIES

The present invention is in the field of medicine, particularly in the novel field of bispecific antibodies directed against Tumor Necrosis Factor alpha (TNFα) and Interleukin-23 (IL-23). The bispecific antibodies of the present invention are expected to be useful in treating autoimmune diseases including Inflammatory Bowel Disease (IBD), such as Crohn's Disease (CD) and Ulcerative Colitis (UC), Axial Spondyloarthropathy (AxSpA), Rheumatoid Arthritis (RA) and Psoriatic Arthritis (PsA).

Autoimmune diseases arise from the body's production of an immune response against its own tissue. Autoimmune diseases are often chronic and can be debilitating and even life-threatening. IBD, which generically represents a group of disorders such as CD and UC, is a common chronic relapsing autoimmune disease characterized pathologically by intestinal inflammation and epithelial injury. Other forms of chronic autoimmune diseases, such as RA, AxSpA and PsA, may affect the axial and/or peripheral skeleton.

Interleukin 23 (IL-23) is a heterodimeric cytokine believed to be important in the activation of a range of inflammatory cells required for the induction of chronic inflammation. IL-23, which is an upstream regulator of IL-6, IL-17, GM-CSF and IL-22 secretion, is composed of a p19 subunit (IL23p19) covalently paired to a p40 subunit (the p40 subunit is shared with cytokine IL-12). Additionally, IL-23 has been implicated as playing an important role in both memory/pathogenic T-cell inflammatory response as well as playing a role in the regulation of innate lymphoid cell inflammatory activity. There is evidence that IL-23 regulation of the cytokines IL-6, IL-17, GM-CSF and IL-22 is associated with inflammatory diseases including IBD, RA and other autoimmune diseases.

Tumor Necrosis Factor alpha (TNFα) is a pleiotropic homotrimeric cytokine which is primarily secreted by monocytes and macrophages, but also known to be produced by $CD4^+$ and $CD8^+$ peripheral blood T lymphocytes. TNFα is expressed in both a soluble and transmembrane form (the membrane-bound precursor form can be proteolytically cleaved into a soluble homotrimer by metalloproteinase TNF alpha converting enzyme (TACE)). TNFα is believed to play a role in the regulation of immune cells and be important in systemic inflammation, specifically in acute phase inflammatory reactions. Excess amounts of TNFα have been associated with various forms of autoimmune diseases, including RA, CD and psoriasis.

Current FDA approved treatments for autoimmune diseases such as IBD include corticosteroids, often used to treat acute inflammation, and bioproducts, many of which (such as REMICADE®, ENBREL® and HUMIRA®) attempt to target and neutralize TNFα in the body. Another bioproduct approved for treatment of PsA includes STELARA® which attempts to target the shared p40 subunit of cytokines IL-12 and IL-23. Current treatments have demonstrated efficacy for reducing symptoms and slowing progression of some autoimmune diseases in a subset of patients. However, a large percentage of patients are nonresponsive to currently available treatments (for example, induction of remission occurs in only 30-50% of CD patients treated with TNFα neutralization, and loss of response to TNFα neutralization occurs in between 23 and 46% of patients following 12 months of treatment). Thus, there remains a need for alternative therapies for treatment of autoimmune diseases, including IBD (such as CD and UC), RA, AxSpA and PsA. Preferably, such alternative therapies will be capable of demonstrating efficacy in a large percentage of patients non-responsive to currently available treatments.

One approach to such alternative therapies may include the co-administration of two different bioproducts (e.g., antibodies). Co-administration requires either injections of two separate products or a single injection of a co-formulation of two different antibodies. While two injections permit flexibility of dose amounts and timing, it is inconvenient to patients both for compliance and pain. Further, while a co-formulation might provide some flexibility of dose amounts, it is often quite challenging or impossible to find formulation conditions having acceptable viscosity in solution (at relatively high concentration) and that permit chemical and physical stability of both antibodies due to different molecular characteristics of the two antibodies. Additionally, co-administration and co-formulation involve the additive costs of two different drug therapies which can increase patient and/or payor costs. Thus, there remains a need for alternative therapies for treatment of autoimmune diseases and preferably such alternative therapies will comprise a bispecific antibody.

U.S. Patent Publication Number 2012/0251541 A1 discloses antibody-like binding proteins having a cross-over dual variable ("CODV") configuration with an antigen binding site to a TNFα target and an antigen binding site to an IL23/IL12 target (e.g., the shared p40 subunit). U.S. Pat. No. 7,872,102 discloses an antibody to the p19 subunit of IL-23 useful in the treatment of autoimmune diseases such as multiple sclerosis. U.S. Pat. No. 6,090,382 discloses human antibodies to human TNFα. WO2011/070339 discloses a method of co-administrating, and a co-formulation of, anti-TNFα and anti-IL-23p40 antibodies for CD, RA, PsA, AxSpA and psoriasis. Despite these disclosures, high affinity neutralizing bispecific antibodies that specifically bind and neutralize both TNFα and the p19 subunit of IL-23 were not described in any of these applications.

Furthermore, significant problems associated with chemical and physical stability were encountered when building a bispecific antibody of the present invention. Many changes were required in the starting bispecific antibody to sufficiently overcome a myriad of issues, such as expressing a physically stable molecule, stabilizing the VH/VL interface of the single chain fragment variable region (scFv), increasing thermal and salt-dependent stability, decreasing aggregation, increasing solubility at high concentrations, and rebalancing the electrostatic distribution in the binding surfaces of the bispecific antibody, all while maintaining binding affinity for both targeted antigens; TNFα and the p19 subunit of IL-23, respectively.

Therefore, a need still exists for a single bispecific antibody that neutralizes both human TNFα and human IL-23, where the bispecific antibody specifically targets the p19 subunit of human IL-23 and does not specifically neutralize IL-12 (which shares a common p40 subunit with IL-23). It is desirable to provide a bispecific antibody that is thermally stable, physically stable, exhibits low aggregation, and neutralizes human TNFα and human IL23p19. It is also desirable to provide a pharmaceutical composition including a single bispecific antibody that neutralizes both human TNFα and human IL23p19, thereby avoiding the challenges of finding formulation conditions that must satisfy the different molecular characteristics of two different, separate antibodies. The present invention therefore seeks to address one or more of the above mentioned problems.

The present invention provides a bispecific antibody having an immunoglobulin G antibody (IgG) that binds tumor necrosis factor alpha (TNFα) conjugated to two single chain variable fragments (scFv) that bind the p19 subunit of IL-23 (IL23p19). According to a bispecific antibody of the present invention, the IgG has two heavy chains (HC) and two light chains (LC), each HC having a heavy chain variable region (HCVR1) with heavy chain complementarity determining regions (HCDR) 1-3 and each LC having a light chain variable region (LCVR1) with light chain complementarity determining regions (LCDR) 1-3. According to a bispecific antibody of the present invention, the amino acid sequence of HCDR1 is SEQ ID NO:9, the amino acid sequence of HCDR2 is SEQ ID NO:10, the amino acid sequence of HCDR3 is SEQ ID NO:11, the amino acid sequence of LCDR1 is SEQ ID NO:15, the amino acid sequence of LCDR2 is SEQ ID NO:16, and the amino acid sequence of LCDR3 is SEQ ID NO:17. The scFv of bispecific antibodies of the present invention have a heavy chain variable region (HCVR2), with HCDRs 4-6, and a light chain variable region (LCVR2) with LCDRs 4-6. According to a bispecific antibody of the present invention the amino acid sequence of HCDR4 is SEQ ID NO:12, the amino acid sequence of HCDR5 is SEQ ID NO:13, the amino acid sequence of HCDR6 is SEQ ID NO:14, the amino acid sequence of LCDR4 is SEQ ID NO:18, the amino acid sequence of LCDR5 is SEQ ID NO:19, and the amino acid sequence of LCDR6 is SEQ ID NO:20. Further, bispecific antibodies of the present invention have each scFv independently conjugated to the IgG antibody via a polypeptide linker (Linker 1 (L1)) covalently attached to the C-terminus of each IgG HC and the N-terminus of HCVR2 of each scFv. Additionally, bispecific antibodies of the present invention have the HCVR2 of each scFv covalently attached to the LCVR2 of the same scFv via a second polypeptide linker (Linker 2 (L2)) covalently attached to the C-terminus of the HCVR2 and the N-terminus of the LCVR2 of the same scFv. According to a bispecific antibody of the present invention, the amino acid sequence of L1 is SEQ ID NO:21 and the amino acid sequence of L2 is SEQ ID NO:22.

The present invention also provides a bispecific antibody having an IgG that binds TNFα conjugated to two scFvs that bind IL23p19, where the IgG has two heavy chains and two light chains, each heavy chain having a heavy chain variable region (HCVR1) and each light chain having a light chain variable region (LCVR1). According to a bispecific antibody of the present invention, the amino acid sequence of HCVR1 is SEQ ID NO: 5 and the amino acid sequence of LCVR1 is SEQ ID NO:7. Additionally, each scFv has a heavy chain variable region (HCVR2) and a light chain variable region (LCVR2). According to a bispecific antibody of the present invention, the amino acid sequence of HCVR2 is SEQ ID NO: 6 and the amino acid sequence of LCVR2 is SEQ ID NO:8. Additionally, each scFv is independently conjugated to the IgG antibody via a polypeptide linker (L1) covalently attached to the C-terminus of each IgG HC and the N-terminus of HCVR2 of each scFv. Further, the HCVR2 of each scFv is covalently attached to the LCVR2 of the same scFv via a second polypeptide linker (L2) covalently attached to the C-terminus of the HCVR2 and the N-terminus of the LCVR2 of the same scFv.

The present invention further provides a bispecific antibody having an IgG that binds TNFα conjugated to two scFvs that bind IL23p19, where the IgG has two HCs and two LCs. According to a bispecific antibody of the present invention, the amino acid sequence of HC is SEQ ID NO:23 and the amino acid sequence of LC is SEQ ID NO:2. Additionally, each scFv has a heavy chain variable region (HCVR2) and a light chain variable region (LCVR2). According to a bispecific antibody of the present invention, the amino acid sequence of HCVR2 is SEQ ID NO: 6 and the amino acid sequence of LCVR2 is SEQ ID NO:8. Additionally, each scFv is independently conjugated to the IgG antibody via a polypeptide linker (L1) covalently attached to the C-terminus of each IgG HC and the N-terminus of HCVR2 of each scFv. Further, the HCVR2 of each scFv is covalently attached to the LCVR2 of the same scFv via a second polypeptide linker (L2) covalently attached to the C-terminus of the HCVR2 and the N-terminus of the LCVR2 of the same scFv. According to a bispecific antibody of the present invention, the amino acid sequence of L1 is SEQ ID NO:21 and the amino acid sequence of L2 is SEQ ID NO:22.

The relationship of the various regions and linkers of an exemplified bispecific antibody of the present invention is as follows (numbering of amino acids applies linear numbering; assignment of amino acids to variable domains is based on the International Immunogenetics Information System® available at www.imgt.org; assignment of amino acids to CDR domains is based on the well-known Kabat and North numbering conventions as reflected in Table 1):

TABLE 1

Amino acid regions of an exemplified bispecific antibody of the present invention.

| SEQ ID NO: 1 | | | SEQ ID NO: 2 | | |
|---|---|---|---|---|---|
| | Region | Positions | | Region | Positions |
| HCVR1 TNFα | FRH1-1 | 1-22 | LCVR1 TNFα | FRL1-1 | 1-23 |
| | HCDR1 | 23-35 | | LCDR1 | 24-34 |
| | FRH1-2 | 36-49 | | FRL1-2 | 35-48 |
| | HCDR2 | 50-66 | | LCDR2 | 49-56 |
| | FRH1-3 | 67-96 | | FRL1-3 | 57-88 |
| | HCDR3 | 97-110 | | LCDR3 | 89-97 |
| | FRH1-4 | 111-121 | | FRL1-4 | 98-107 |
| Constant | CH | 122-449 | Constant | CL | 108-214 |
| Linker | L1 | 450-464 | | | |
| HCVR2 IL-23 | FRH2-1 | 465-486 | | | |
| | HCDR4 | 487-499 | | | |
| | FRH2-2 | 500-513 | | | |
| | HCDR5 | 514-530 | | | |
| | FRH2-3 | 531-560 | | | |
| | HCDR6 | 561-568 | | | |
| | FRH2-4 | 569-579 | | | |
| Linker | L2 | 580-599 | | | |
| LCVR2 IL-23 | FRL2-1 | 600-622 | | | |
| | LCDR4 | 623-633 | | | |
| | FRL2-2 | 634-647 | | | |
| | LCDR5 | 648-655 | | | |
| | FRL2-3 | 656-687 | | | |
| | LCDR6 | 688-696 | | | |
| | FRL2-4 | 697-706 | | | |

| CDR | Starting Amino Acid Pos. Definition | Ending Amino Acid Pos. Definition |
|---|---|---|
| HCDR1 | North | Kabat |
| HCDR2 | Kabat | Kabat |
| HCDR3 | North | Kabat |
| HCDR4 | North | Kabat |
| HCDR5 | Kabat | Kabat |
| HCDR6 | North | Kabat |
| LCDR1 | Kabat | Kabat |
| LCDR2 | North | Kabat |
| LCDR3 | Kabat | Kabat |
| LCDR4 | Kabat | Kabat |
| LCDR5 | North | Kabat |
| LCDR6 | Kabat | Kabat |

The present invention further provides a bispecific antibody wherein each of the HCs form an inter-chain disulfide bond with each of the LCs; wherein each of the HCs forms an inter-chain disulfide bond with the other HC; and wherein each of the scFvs forms an intra-chain disulfide bond between HCVR2 and LCVR2. According to the exemplified bispecific antibody of the present invention presented in Table 1, an inter-chain disulfide bond of each of the HCs and each of the LCs forms between cysteine residue 148 (of SEQ ID NO:1) of the HC, and cysteine residue 214 (of SEQ ID NO:2) of the LC; at least two inter-chain disulfide bonds form between the two HCs, the first inter-chain disulfide bond forming between cysteine residue 230 (of SEQ ID NO: 1) of the HC and cysteine residue 230 (of SEQ ID NO: 1) of the other HC, the second inter-chain disulfide bond forming between cysteine residue 233 (of SEQ ID NO: 1) of the HC and cysteine residue 233 (of SEQ ID NO: 1) of the other HC; and an intra-chain disulfide bond of the scFv is formed between cysteine residue 508 (of SEQ ID NO: 1) of the HCVR2 and cysteine residue 699 (of SEQ ID NO:1) of the LCVR2.

According to some embodiments of the present invention, a bispecific antibody comprising glycosylation of the HC is provided. According to the exemplified bispecific antibody of the present invention presented in Table 1, glycosylation of the HC occurs at the asparagine residue 301 of SEQ ID NO: 1.

The present invention also provides a DNA molecule comprising a polynucleotide sequence encoding a polypeptide chain comprising a HC, scFv, L1 and L2 of the bispecific antibody of present invention. According to an embodiment of the present invention, the amino acid sequence of the encoded polypeptide chain is SEQ ID NO:1.

The present invention also provides a DNA molecule comprising a polynucleotide sequence encoding a second polypeptide chain comprising a LC of the bispecific antibody of the present invention. According to an embodiment of the present invention, the amino acid sequence of the second encoded polypeptide chain is SEQ ID NO:2.

The present invention also provides a DNA molecule comprising a polynucleotide sequence encoding a polypeptide chain comprising a HC, a scFv, L1 and L2 of the bispecific antibody of present invention, and comprising a second polynucleotide sequence encoding a second polypeptide chain comprising a LC of the bispecific antibody of the present invention. According to an embodiment of the present invention, the amino acid sequence of the encoded polypeptide chain comprising a HC, scFv, L1 and L2 is SEQ ID NO:1 and an expression vector containing the DNA sequence of SEQ ID NO: 3 encodes the polypeptide chain. Also, according to an embodiment of the present invention, the amino acid sequence of the second encoded polypeptide chain is SEQ ID NO:2 and an expression vector containing the DNA sequence of SEQ ID NO: 4 encodes the second polypeptide chain.

The present invention also provides a mammalian cell comprising a DNA molecule of the present invention, wherein the cell is capable of expressing a bispecific antibody of the present invention, said bispecific antibody comprising an IgG that binds TNFα conjugated to two scFvs that bind IL23p19.

The present invention also provides a mammalian cell transformed with a DNA molecule(s) of the present invention, wherein the cell is capable of expressing a bispecific antibody of the present invention, said bispecific antibody comprising an IgG that binds TNFα conjugated to two scFvs that bind IL23p19.

The present invention also provides a process for producing a bispecific antibody of the present invention, the process comprising cultivating a mammalian cell of the present invention under conditions such that the bispecific antibody is expressed, and recovering the expressed bispecific antibody. The present invention also provides a bispecific antibody according to the present invention produced by said process.

The present invention also provides a method of treating autoimmune diseases comprising administering to a patient in need thereof an effective amount of a bispecific antibody of the present invention.

The present invention also provides a method of treating IBD, such as CD and UC, comprising administering to a patient in need thereof a therapeutically effective amount of a bispecific antibody of the present invention.

The present invention also provides a method of treating RA, AxSpA and PsA comprising administering to a patient in need thereof a therapeutically effective amount of a bispecific antibody of the present invention.

The present invention also provides a bispecific antibody of the present invention for use in therapy.

The present invention also provides a bispecific antibody of the present invention for use in the treatment of autoimmune diseases including IBD, such as CD and UC.

The present invention also provides a bispecific antibody of the present invention for use in the treatment of autoimmune diseases including RA, AxSpA and PsA.

The present invention also provides a pharmaceutical composition comprising a bispecific antibody of the present invention and one or more pharmaceutically acceptable carriers, diluents or excipients.

Another embodiment of the present invention comprises use of a bispecific antibody of the present invention in the manufacture of a medicament for the treatment of ulcerative colitis and Crohn's disease.

An additional embodiment of the present invention comprises use of a bispecific antibody of the present invention in the manufacture of a medicament for the treatment of rheumatoid arthritis, psoriatic arthritis, and axial spondyloarthropathy.

DEFINITIONS

When used herein the term "bispecific antibody" refers to a molecule comprising an immunoglobulin G antibody (IgG) conjugated to two single chain variable fragments (scFv). As referred to herein, a bispecific antibody of the present invention comprises one scFv covalently linked to the carboxy-terminus of a HC of the IgG by a polypeptide linker (L1) and the other scFv covalently linked to the carboxy-terminus of the other HC of the IgG by a polypeptide linker (L1). The IgG and scFvs of a bispecific antibody of the present invention specifically bind different antigens (TNFα and the p19 subunit of IL-23, respectively).

When used herein, the term "immunoglobulin G antibody" (IgG), refers to an immunoglobulin molecule comprised of four polypeptide chains; two heavy chains (HC) and two light chains (LC) interconnected by disulfide bonds. The amino-terminal portion of each of the four polypeptide chains includes a variable region of about 100-110 or more amino acids primarily responsible for antigen recognition. The carboxy-terminal portion of each of the four polypeptide chains defines a constant region primarily responsible for effector function. The carboxy-terminal portion of each heavy chain is covalently attached to one of the single chain variable fragments (scFv) via a polypeptide linker (L1).

The light chains (LC) of the IgG of the bispecific antibody of the present invention are classified as kappa or lambda and characterized by a particular constant region as known in the art. The heavy chains (HC) of the IgG according to the present invention is classified as gamma, which defines the isotype (e.g., as an IgG). The isotype may be further divided into subclasses (e.g., IgG$_1$, IgG$_2$, IgG$_3$, and IgG$_4$). Each HC type is characterized by a particular constant region known in the art. Each HC is comprised of an N-terminal heavy chain variable region ("HCVR") and a heavy chain constant region (CH). The CH for IgG, according to the present invention, is comprised of three domains (CH1, CH2, and CH3). Each light chain of the IgG is comprised of a light chain variable region (LCVR) and a light chain constant region (CL). The HCVR and LCVR regions can be further subdivided into regions of hypervariability, termed complementarity determining regions (CDRs), interspersed with regions that are more conserved, termed framework regions (FR). Each HCVR and LCVR of the IgGs according to the present invention are composed of three CDRs and four FRs, arranged from amino-terminus to carboxy-terminus in the following order: FR1-1, CDR1, FR1-2, CDR2, FR1-3, CDR3, FR1-4. Herein the 3 CDRs of the HC are referred to as "HCDR1, HCDR2 and HCDR3" and the 3 CDRs of the LC are referred to as "LCDR1, LCDR2 and LCDR3." The CDRs contain most of the residues which form specific interactions with the antigen. The functional ability of an antibody to bind a particular antigen is largely influenced by the six CDRs.

As referred to herein, the term "single chain variable fragment" (scFv), refers to a polypeptide chain comprising a heavy chain variable region (HCVR2) and a light chain variable region (LCVR2) connected via a polypeptide linker (L2). Additionally, as referred to herein (and as represented in the following schematic), the HCVR2 of each scFv is: a.) covalently linked, at its N-terminus, to the C-terminus of one HC of the IgG via a polypeptide linker (L1); and b.) covalently linked, at its C-terminus, to the N-terminus of the LCVR2 of the same scFv via a second polypeptide linker (L2). Further, each scFv of the present invention includes a disulfide bond formed between a cysteine residue of HCVR2 and a cysteine residue of LCVR2 of the same polypeptide chain (as represented in the following schematic):

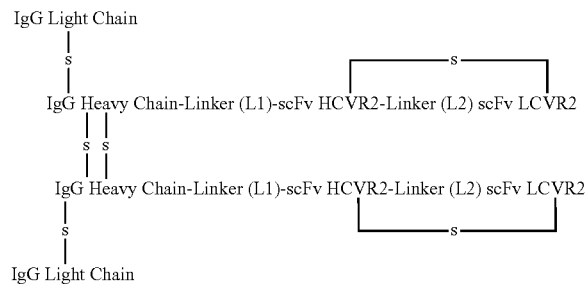

HCVR2 and LCVR2 of the scFv can be further subdivided into regions of hypervariability, termed complementarity determining regions (CDRs), interspersed with regions that are more conserved, termed framework regions (FR). Each HCVR2 and LCVR2 of the IgGs according to the present invention are each composed of three CDRs and four FRs, arranged from amino-terminus to carboxy-terminus in the following order: FR2-1, CDR4, FR2-2, CDR5, FR2-3, CDR6, FR2-4. Herein the 3 CDRs of HCVR2 of the scFv are referred to as "HCDR4, HCDR5 and HCDR6" and the 3 CDRs of LCVR2 of the scFv are referred to as "LCDR4, LCDR5 and LCDR6." The CDRs contain most of the residues which form specific interactions with the antigen. The functional ability of a scFv to bind a particular antigen is largely influenced by the six CDRs.

The variable regions of each light/heavy chain pair of an IgG and scFv, respectively, according to the present invention form an antigen-binding site of the bispecific antibody. According to the present invention, the IgG has two antigen binding sites which are the same (but are different than the antigen binding sites of the scFv) and each scFv has an antigen binding site (which is the same as the antigen binding site of the other scFv). As used herein, the "antigen-binding portion" or "antigen-binding site" or "antigen-binding region" or "antigen-binding fragment" refers interchangeably to that portion of an IgG or scFv molecule, within the variable region, which contains the amino acid residues that interact with an antigen and confer to the bispecific antibody specificity and affinity for an antigen. This antibody portion includes the framework amino acid residues necessary to maintain the proper conformation of the antigen-binding residues. Preferably, the framework regions of the bispecific antibodies of the invention are of human origin or substantially of human origin.

A "parent antibody" or "parental antibody," as used interchangeably herein, is an antibody encoded by an amino acid sequence which is used in the preparation of one of the IgG and scFv of the bispecific antibody, for example through amino acid substitutions and structural alteration. The parent antibody may be a murine, chimeric, humanized or human antibody.

The terms "Kabat numbering" or "Kabat labeling" are used interchangeably herein. These terms, which are recognized in the art, refer to a system of numbering amino acid residues which are more variable (i.e., hypervariable) than other amino acid residues in the heavy and light chains variable regions of an antibody (Kabat, et al., *Ann. NY Acad. Sci.* 190:382-93 (1971); Kabat et al., *Sequences of Proteins of Immunological Interest*, Fifth Edition, U.S. Department of Health and Human Services, NIH Publication No. 91-3242 (1991)).

The terms "North numbering" or "North labeling" are used interchangeably herein. These terms, which are recognized in the art, refer to a system of numbering amino acid residues which are more variable (i.e., hypervariable) than other amino acid residues in the heavy and light chains variable regions of an antibody and is based, at least in part, on affinity propagation clustering with a large number of crystal structures, as described in (North et al., *A New Clustering of Antibody CDR Loop Conformations*, Journal of Molecular Biology, 406:228-256 (2011).

The terms "patient," "subject," and "individual," used interchangeably herein, refer to an animal, preferably the term refers to humans. In certain embodiments, the subject, preferably a human, is further characterized with a disease or disorder or condition (e.g., an autoimmune disorder) that would benefit from a decreased level or decreased bioactivity of both IL-23 and TNFα. In another embodiment the subject, preferably a human, is further characterized as being at risk of developing a disorder, disease or condition that would benefit from a decreased level or decreased bioactivity of both IL-23 and TNFα.

Bispecific Antibody Engineering

Significant problems associated with chemical and physical stability were encountered when constructing a bispecific antibody of the present invention. Problems encountered included poor to no expression, poor purification recovery, low thermostability, high salt-dependent aggregation, diabody formation (and challenges in reducing diabodies through purification), high solution viscosity, low binding affinity and cross-reactivity.

For example, initial attempts in constructing a bispecific antibody according to the present invention included constructs in which a parental IL-23 antibody (the IL-23 antibody described in U.S. Pat. No. 7,872,102) comprised the IgG antibody portion and a parental TNFα antibody (Adalimumab, see for example U.S. Pat. No. 6,090,382) comprised the scFv portion of the bispecific antibody. Other initially attempted constructs included the parental IL-23 antibody comprising the scFv portion while the TNFα antibody comprised the IgG portion of the bispecific antibody. Additionally, initial constructs included the scFv portion being conjugated to the IgG portion in various configurations, including at the amino-terminus or the carboxyl terminus for both the heavy and light chains, respectively. Also, initial constructs included the scFv portion varying in arrangement of the HCVR2 and LCVR2 (e.g., IgG portion (C or N terminus)—linker 1—LCVR2 or HCVR2—linker 2—the other of LCVR2 or HCVR2). Further, parental IL-23 antibody constructs included combinations of heavy chain germline frameworks VH 5-51 and 1-69, and light chain germline frameworks VK 02, VK 12 and VK B3. Parental TNFα antibody constructs (when comprising the IgG portion) included an IgG4 subclass structure having three amino acid mutations (from native IgG4) within the constant region (CH). Initial constructs were cloned into a human IgG4-Fc mammalian expression vector. However, initially produced bispecific constructs as (described above) exhibited one or more chemical and/or physical problem(s) described above.

Electrostatic surface of the bispecific antibody was calculated and charged patches were identified and disrupted. Extensive protein stability studies were performed and the constructed bispecific antibodies were screened for thermostability properties as well as TNFα and IL-23 binding (relative to the respective parental antibody) properties.

Chemical and physical modifications were therefore made to improve chemical and physical stability of the bispecific antibody of the present invention. Modifications to the parental IL-23 antibody, in scFv format, were made in HCDR4, HCDR5, LCDR4, LCDR5 and LCDR6 to improve chemical and physical stability. Constructed HCVR and LCVR were combined into the IL-23 scFv format according to the following formula: TNFα IgG (C-term.)—L1—HCVR2—L2—LCVR2. A disulfide bond, for stabilizing the IL-23 scFv, was engineered between the HCVR2 (G508C) and the LCVR2 (G699C) of the IL-23 scFv (numbering of amino acids applies linear numbering based on exemplified bispecific antibody presented in Table 1). Additionally, the parental TNFα antibody, in an IgG portion of the bispecific antibody, was engineered to an IgG1 subclass for improved biochemical behavior, including solubility and reduced aggregation. The engineered IL-23 scFv construct and TNFα IgG construct, comprising these chemical and physical modifications, were inserted into an IgG1 expression vector.

A bispecific antibody containing a TNFα IgG, as an IgG1 subclass, and an IL-23 scFv with six CDR mutations (relative to the parental IL-23 antibody: HCVR at K28P and T54V; and LCVR at L30G, L53K, E54L and M90Q, assignment of amino acid numbering is based on the well-known Kabat numbering conventions)(as represented in the exemplified bispecific antibody reflected in Table 1: HCVR at K492P and T522V; and LCVR at L629G, L653K, E654L and M689Q, numbering of amino acids is based on linear numbering) was identified as improving the expression, affinity (for IL-23 relative to the parental molecule) and thermostability issues demonstrated in initial constructs. Additionally, these mutations resulted in a significantly reduced clearance rate in cynolomolgus monkeys. None of the above modifications were identified in initial characterizations of the parental single antibodies.

Bispecific Antibody Binding

The bispecific antibodies of the present invention bind both human TNFα and human IL23p19 and neutralize at least one human TNFα bioactivity and at least one human IL-23 bioactivity in vitro or in vivo. The bispecific antibodies of the present invention are potent inhibitors of IL-23 in the presence and absence of TNFα in vitro. The bispecific antibodies of the present invention are potent inhibitors of both soluble and membrane-bound TNFα in the presence or absence of IL-23 in vitro.

The bispecific antibodies of the invention are further characterized as having a binding affinity ($K_D$) for human TNFα in the range of 96±3.5 pM and human IL23p19 in the range of 121±8.5 pM at 37° C. The bispecific antibodies effectively neutralize soluble as well as membrane-bound TNFα and this neutralization is not affected by the presence of saturating amounts of human IL-23. The bispecific antibodies effectively neutralize human IL-23 and this neutralization is not affected by the presence of saturating amounts of human TNFα.

Bispecific Antibody Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. The first polypeptide chain (comprising a HC, scFv, L1 and L2) and the second polypeptide chain (comprising a LC) may be expressed independently from different promoters to which they are operably linked in one vector or, alternatively, the first and second polypeptide chains may be expressed independently from different promoters to which they are operably linked in two vectors—one expressing the first polypeptide chain and one expressing the second polypeptide chain.

A host cell includes cells stably or transiently transfected, transformed, transduced or infected with one or more expression vectors expressing a first polypeptide chain, a second polypeptide chain or both a first and a second polypeptide chain of the invention. Creation and isolation of host cell lines producing a bispecific antibody of the invention can be accomplished using standard techniques known in the art. Mammalian cells are preferred host cells for expression of bispecific antibodies. Particular mammalian cells are HEK 293, NS0, DG-44, and CHO. Preferably, the bispecific antibodies are secreted into the medium in which the host cells are cultured, from which the bispecific antibodies can be recovered or purified.

It is well known in the art that mammalian expression of antibodies results in glycosylation. Typically, glycosylation occurs in the Fc region of the antibody at a highly conserved N-glycosylation site. N-glycans typically attach to asparagine. By way of example, each HC of exemplified bispecific antibody presented in Table 1 is glycosylated at asparagine residue 301 of SEQ ID NO:1.

A particular DNA polynucleotide sequence encoding a first polypeptide chain (comprising a HC, scFv, L1 and L2 of the present invention and having an amino acid sequence of SEQ ID NO:1) is:

(SEQ ID NO: 3)
atggagacagacacactcctgctatgggtactgctgctctgggttcc aggctccactggcgaggtgcagctggtggagtctgggggaggcttgg tacagcctggggaggtccctgagactctcctgtgcagcctctggattc acctttgatgactatgccatgcactgggtccgccaggctccaggaa ggggctggagtgggtgtcagctattacttggaatagtggtcacatag actacgcagactccgtggagggccggttcaccatctccagagacaat gccaagaactccctgtatctgcaaatgaacagcctgagagccgagga cacggccgtatattactgtgcgaaagtgagctacctgagtactgcct ccagcctggactactggggccaaggaaccctggtcaccgtctcctca gcctccaccaagggcccatcggtcttccccgctagcaccctcctccaa gagcacctctgggggcacagcggccctgggctgcctggtcaaggact acttccccgaaccggtgacggtgtcgtggaactcaggcgccctgacc agcggcgtgcacaccttcccggctgtcctacagtcctcaggactcta ctccctcagcagcgtggtgaccgtgccctccagcagcttgggcaccc agacctacatctgcaacgtgaatcacaagcccagcaacaccaaggtg gacaagaaagttgagcccaaatcttgtgacaaaactcacacatgccc accgtgcccagcacctgaactcctggggggaccgtcagtcttcctct tccccccaaaacccaaggacaccctcatgatctcccggacccctgag gtcacatgcgtggtggtggacgtgagccacgaagaccctgaggtcaa gttcaactggtacgtggacggcgtggaggtgcataatgccaagacaa agccgcgggaggagcagtacaacagcacgtaccgtgtggtcagcgtc ctcaccgtcctgcaccaggactggctgaatggcaaggagtacaagtg caaggtctccaacaaagccctcccagcccccatcgagaaaaccatct ccaaagccaaagggcagccccgagaaccacaggtgtacaccctgccc ccatcccgggacgagctgaccaagaaccaggtcagcctgacctgcct ggtcaaaggcttctatcccagcgacatcgccgtggagtgggagagca atgggcagccggagaacaactacaagaccacgcccccgtgctggac tccgacggctccttcttcctctatagcaagctcaccgtggacaagag caggtggcagcaggggaacgtcttctcatgctccgtgatgcatgagg ctctgcacaaccactacacgcagaagagcctctccctgtctccggt ggcggaggctccggggggagggggtagcggaggagggggatcccaggt gcagctggtgcagtctgggctgaggtgaagaagcctgggtcctcgg tgaaggtctcctgcaaggcttctggatatccattcactcgctatgtt atgcactgggtgcgacaggcccctggacaatgccttgagtggatggg atatattaatcctacaatgatggtgtgaactacaatgagaagttca aaggcagagtcacgattaccgcggacgaatccacgagcacagcctac atggagctgagcagcctgagatctgaggacacggccgtgtattactg tgcgagaaactgggacacaggcctctgggggcaagggaccacggtca ccgtctcctcaggcggcggaggctctggcggaggtggtagtggtggc ggtggatcaggggaggcggatctgacatccagatgacccagtctcc -continued atcctccctgtctgcatctgtaggagacagagtcaccatcacttgca aggcaagtgaccacattggcaaatttttaacttggtatcagcagaaa ccagggaaagcccctaagctcctgatctatggtgcaaccagcaagct gactgggtcccatcaaggttcagtggcagtggatctgggacagatt tcactctcaccatcagcagtctgcaacctgaagattttgcaacttac tactgtcaacagtattggagtactccgttcacgttcggatgcgggac caaggtggaaataaaa.

A particular DNA polynucleotide sequence encoding a second polypeptide chain (comprising a LC of the present invention having an amino acid sequence of SEQ ID NO:2) is:

(SEQ ID NO: 4)
atggagacagacacactcctgctatgggtactgctgctctgggttcc aggatccactggcgacatccagatgacccagtctccatcctccctgt ctgcatctgtaggagacagagtcaccatcacttgccgggcgagtcag ggcattcgcaattatttagcctggtatcagcagaaaccagggaaagc tcctaagctcctgatctatgctgcatccacttttgcaatcaggggtcc catctcggttcagtggcagtggatctgggacagatttcactctcacc atcagcagcctgcagcctgaagatgttgcaacttattactgtcaacg ctataaccgtgccccttacacgttcggccaagggaccaaggtggaaa tcaaacggactgtggctgcaccatctgtcttcatcttcccgccatct gatgagcagttgaaatctggaactgcctctgttgtgtgcctgctgaa taacttctatcccagagaggccaaagtacagtggaaggtggataacg ccctccaatcgggtaactcccaggagagtgtcacagagcaggacagc aaggacagcacctacagcctcagcagcaccctgacgctgagcaaagc agactacgagaaacacaaagtctacgcctgcgaagtcacccatcagg gcctgagctcgcccgtcacaaagagcttcaacaggggagagtgc.

Medium, into which a bispecific antibody has been secreted, may be purified by conventional techniques. For example, the medium may be applied to and eluted from a Protein A or G column using conventional methods. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

In some instances, process for producing a bispecific antibody of the present invention may result in the formation of diabodies. Diabodies are bivalent formations of scFv in which HCVR2 and LCVR2 regions are expressed on a single polypeptide chain, but instead of the variable domains pairing with complementary domains of the same polypeptide chain, the variable domains pair with complementary domains of the other polypeptide chain or a different molecule. For example, if the bispecific antibody comprises two first polypeptides (for convenience, 1A and 1B, where each of 1A and 1B comprise a HC, a scFv, L1 and L2), and two second polypeptides (for convenience, 2A and 2B, where each of 2A and 2B comprise a LC), HCVR2 of 1A pairs with complementary domains of LCVR2 of 1B instead of pairing with LCVR2 of 1A. As described herein, it may be beneficial to purify out diabodies from the bispecific antibodies described above. Diabody content can be greater than 10% after cellular expression and can be reduced to less than 3% after purification.

Therapeutic Uses

As used herein, "treatment" and/or "treating" are intended to refer to all processes wherein there may be a slowing, interrupting, arresting, controlling, or stopping of the progression of the disorders described herein, but does not necessarily indicate a total elimination of all disorder symptoms. Treatment includes administration of a bispecific antibody of the present invention for treatment of a disease or condition in a mammal, particularly in a human, that would benefit from a decreased level of TNFα and/or IL-23 or decreased bioactivity of TNFα and/or IL-23, and includes: (a) inhibiting further progression of the disease, i.e., arresting its development; and (b) relieving the disease, i.e., causing regression of the disease or disorder or alleviating symptoms or complications thereof.

The bispecific antibody of the present invention is expected to treat autoimmune diseases, including IBD (such as CD and UC), AxSpA, RA and PsA.

Pharmaceutical Composition

A bispecific antibody of the invention can be incorporated into a pharmaceutical composition suitable for administration to a patient. A bispecific antibody of the invention may be administered to a patient alone or with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., Remington, *The Science and Practice of Pharmacy*, 22$^{nd}$ Edition, Loyd V, Ed., Pharmaceutical Press, 2012, which provides a compendium of formulation techniques as are generally known to practitioners. Suitable carriers for pharmaceutical compositions include any material which, when combined with a bispecific antibody of the invention, retains the molecule's activity and is non-reactive with the patient's immune system. A pharmaceutical composition of the present invention comprises a bispecific antibody and one or more pharmaceutically acceptable carriers, diluents or excipients.

A pharmaceutical composition comprising a bispecific antibody of the present invention can be administered to a patient at risk for or exhibiting diseases or disorders as described herein using standard administration techniques.

A pharmaceutical composition of the invention contains an "effective" or "therapeutically effective" amount, as used interchangeably herein, of a bispecific antibody of the invention. An effective amount refers to an amount necessary (at dosages and for periods of time and for the means of administration) to achieve the desired therapeutic result. An effective amount of the bispecific antibody may vary according to factors such as the disease state, age, sex, and weight of the individual, and the ability of the antibody or antibody portion to elicit a desired response in the individual. An effective amount is also one in which any toxic or detrimental effect of the bispecific antibody, are outweighed by the therapeutically beneficial effects.

EXAMPLES

Except as noted otherwise, the exemplified bispecific antibody referred to throughout the Examples refers to the exemplified bispecific antibody of the present invention set forth in Table 1 above.

Bispecific Antibody Expression and Purification

The exemplified bispecific antibody is expressed and purified essentially as follows. A glutamine synthetase (GS) expression vector containing the DNA of SEQ ID NO:3 (encoding a polypeptide chain, comprising the IgG HC, the scFv HCVR2 and LCVR2 and linkers L1 and L2, and having the amino acid sequence of SEQ ID NO:1) and SEQ ID NO:4 (encoding a second polypeptide chain, comprising the IgG LC, and having the amino acid sequence of SEQ ID NO:2) is used to transfect a Chinese hamster cell line, CHO (GS knockout, clone 1D3), by electroporation. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for bispecific antibody expression and then scaled up in serum-free, suspension cultures to be used for production. Clarified medium, into which the exemplified bispecific antibody has been secreted, is applied to a Protein A affinity column that has been equilibrated with a compatible buffer such as phosphate buffered saline (pH 7.4). The column is washed to remove nonspecific binding components. The bound bispecific antibody is eluted, for example, by pH gradient (such as 0.1 M sodium phosphate buffer pH 6.8 to 0.1 M sodium citrate buffer pH 2.5) and neutralized with Tris, pH 8 buffer. Bispecific antibody fractions are detected, such as by SDS-PAGE or analytical size-exclusion, and then are pooled. Soluble aggregate and multimers may be effectively removed by common techniques including size exclusion, hydrophobic interaction, ion exchange, or hydroxyapatite chromatography. The bispecific antibody is concentrated and/or sterile filtered using common techniques. The purity of the exemplified bispecific antibody after these chromatography steps is greater than 98.6% (monomer). The bispecific antibody may be immediately frozen at −70° C. or stored at 4° C. for several months.

Bispecific Antibody Solubility and Stability Analysis

The exemplified bispecific antibody is formulated in 10 mM citrate pH 6.0. The bispecific antibody is concentrated to 1 mg/mL, 50 mg/mL and 100 mg/mL (using Amicon U.C. filters, Millipore, catalog # UFC903024). Samples concentrated to 1 mg/mL are incubated at one of 4 and 25° C. over a period of 4 weeks and samples concentrated to 50 and 100 mg/mL are incubated with 25 or 150 mM NaCl at one of 4 and 25° C. over a period of 4 weeks.

Following incubation, samples are analyzed for percent high molecular weight (% HMW) with size exclusion chromatography (SEC) using a TSKgel Super SW3000 (Tosoh Bioscience product #18675) column 50 mM sodium phosphate+350 mM NaCl, pH 7.0 is used as the mobile phase running at 0.4 mL/min for 15 minutes. A volume of 5 µL (5 µg) of the concentrated antibody is injected into the column and the detection is measured at 214 nm. For high concentration samples, a volume of 1 µL (50 µg or 100 µg) is injected into the column and the detection is measured at 280 nm. Chromatograms are analyzed using ChemStation and % high molecular weight (HMW) is calculated using the ratio of AUC of the peaks eluted before the monomer peak to total AUC. Results are summarized in Table 2.

TABLE 2

Summary of change in percentage of high molecular weight species from starting control over 4 weeks measured by SE-HPLC.

| Sample Concentration | Incubation Temperature | Change in % of HMW by SE-HPLC |
|---|---|---|
| 1 mg/mL | 4° C. | 0 |
| 1 mg/mL | 25° C. | 0.5 |
| 50 mg/mL | 4° C. | 0.2 |
| 50 mg/mL | 25° C. | 0.7 |
| 100 mg/mL | 4° C. | 0.1 |
| 100 mg/mL | 25° C. | 0.7 |

Sample degradation of samples concentrated to 1 mg/mL is also analyzed with capillary isoelectric focusing (cIEF) analysis using a Beckman-PA800 plus system according to manufacturer instructions. Results are summarized in Table 3.

TABLE 3

Summary of change in sample degradation over 4 weeks measured by cIEF.

| Sample Concentration | Incubation Temperature | % Sample Degradation |
|---|---|---|
| 1 mg/mL | 4° C. | 0.7 |
| 1 mg/mL | 25° C. | 1.7 |

Samples concentrated to 1 mg/mL and stored at 40° C. are also analyzed for identification of peptide bond cleavage with liquid chromatography-mass spectrometry (LC-MS) analysis using a Thermo Scientific Ion Trap LC-MS system according to manufacturer instructions. No region of the bispecific antibody demonstrated peptide bond cleavage of greater than 2%. Only the hinge region (1.8%) and linker L1 (1.1%) of the first encoded polypeptide chain (SEQ ID NO:1 of the exemplified bispecific antibody) demonstrated peptide bond cleavage of greater than 1%.

Solubility of the exemplified bispecific antibody is analyzed at 4, −5 and −10° C. after one week incubation period. Solubility is assessed with bispecific antibody concentrated to between 100 and 150 mg/mL (using Amicon U.C. filters, Millipore, catalog # UFC903024) and formulated in 10 mM citrate at pH 6.0 including 150 mM NaCl. The exemplified bispecific antibody exhibited good solubility and lacked phase separation following the incubation period.

Viscosity of the exemplified bispecific antibody is analyzed at room temperature. Viscosity is assessed with bispecific antibody concentrated to 100 mg/mL (using Amicon U.C. filters, Millipore, catalog # UFC903024) and formulated in 10 mM citrate at pH 6.0 including 150 mM NaCl. The exemplified bispecific antibody exhibited good viscosity, 4.2 cp at 100 mg/mL, whereas other initial attempted constructs demonstrated unacceptably high viscosity (>9 cP).

Preliminary studies with a bispecific antibody comprising parental TNFα antibody and parental IL-23 were not possible due to poor bispecific antibody expression, bispecific antibody degradation/clipping, unacceptably high solution viscosity at relatively high concentrations and low affinity (relative to the parental antibodies). However, preliminary studies with the exemplified bispecific antibody of the present invention demonstrate unexpected beneficial properties, including expression of the bispecific antibody and unexpected beneficial chemical and physical stability and solubility properties. As demonstrated by the preliminary data, the bispecific antibody of the present invention exhibits low HMW aggregation, good solubility, good viscosity in solution, increased physical stability including low degradation levels and low peptide bond cleavage, and maintains affinity for both TNFα and the p19 subunit of IL-23.

Bispecific Antibody Binding Affinity to IL-23 and TNFα

Binding affinity and binding stoichiometry of the exemplified bispecific antibody to human IL-23 and human TNFα is determined using a surface plasmon resonance assay on a Biacore T100 instrument primed with HBS-EP+(10 mM Hepes pH7.4+150 mM NaCl+3 mM EDTA+0.05% (w/v) surfactant P20) running buffer and analysis temperature set at 37° C. A CM5 chip (Biacore P/N BR-100530) containing immobilized protein A (generated using standard NHS-EDC amine coupling) on all four flow cells (Fc) is used to employ a capture methodology. Antibody samples are prepared at 10 μg/mL by dilution into running buffer. Human IL-23 are prepared at final concentrations of 20.0, 10.0, 5.0, 2.5, 1.25, 0.62 and 0 (blank) nM by dilution into running buffer. Human TNFα are prepared at final concentrations of 50.0, 25.0, 12.5, 6.25, 3.12, 1.56, 0.78, 0.39, 0.19 and 0 (blank) nM by dilution into running buffer.

Each analysis cycle consists of (1) capturing antibody samples on separate flow cells (Fc2 and Fc3); (2) injection of each human IL-23 concentration over all Fc at 80 μL/min for 200 seconds followed by return to buffer flow for 1800 seconds to monitor dissociation phase; (3) injection of each human TNFα concentration over all Fc at 50 μL/min for 250 seconds followed by return to buffer flow for 1200 seconds to monitor dissociation phase; (4) regeneration of chip surfaces with injection of 10 mM glycine, pH 1.5, for 60 seconds at 80 μL/min over all cells; and (5) equilibration of chip surfaces with a 10 μL (60-sec) injection of HBS-EP+. Data are processed using standard double-referencing and fit to a 1:1 binding model using Biacore T100 Evaluation software, version 2.0.3, to determine the association rate ($k_{on}$, $M^{-1}$ $s^{-1}$ units), dissociation rate ($k_{off}$, $s^{-1}$ units), and $R_{max}$ (RU units). The equilibrium dissociation constant ($K_D$) is calculated from the relationship $K_D = k_{off}/k_{on}$, and is in molar units.

TABLE 4

Binding affinity to human IL-23 and human TNFα by the exemplified bispecific antibody at 37° C.

| Antigen | $k_{on}$ Avg ± SD $M^{-1}s^{-1}$ | $k_{off}$ Avg ± SD $s^{-1}$ ($10^{-4}$) | $K_D$ Avg ± SD pM | n |
|---|---|---|---|---|
| Human IL-23 | 8.3 (±0.8) × $10^5$ | 1.0 ± 0.0 | 121 ± 8.5 | 3 |
| Human TNFα | 4.1 (±0.2) × $10^6$ | 4.0 ± 0.2 | 96 ± 3.5 | 3 |

These results demonstrate that the exemplified bispecific antibody of the present invention binds human IL-23 and human TNFα with high affinity at 37° C.

Simultaneous Binding of IL-23 and TNFα

A BIAcore T100 instrument is used to determine whether human IL-23 and human TNFα can bind to the bispecific antibody simultaneously. Except as noted, all reagents and materials are purchased from BIAcore AB (Upsala, Sweden). All measurements are performed at 37° C. HBS-EP+ buffer (150 mM sodium chloride, 3 mM EDTA, 0.05% (w/v) surfactant P-20, and 10 mM HEPES, pH7.4) is used as the running buffer and sample buffer. Protein A is immobilized on flow cells 1 and 2 of a CM5 sensor chip using an amine coupling kit. The exemplified bispecific antibody (diluted to 1 μg/ml) is first captured on flow cell 2 (with a 4 second injection at 80 µl/min, yielding 95.3 response units (Δ RU) of bispecific antibody capture), followed by injection of human TNFα at 100 nM for 5 min to saturate TNFα binding site (a binding signal of 32.4 Δ RU is observed). Flow cell 1 is a protein A only control. After binding of TNFα (flow cell 2), human IL-23 at 100 nM is then injected for 5 min and additional binding signal (of 57.3 Δ RU) is observed. Chip surface is then regenerated using 10 mM Glycine pH 1.5. The same process is repeated except with a reverse order of human IL-23 first followed by human TNFα. These results demonstrate that the exemplified bispecific antibody of the present invention can bind human IL-23 and human TNFα simultaneously as shown by the increase in response units (initial 32.4 RU from TNFα and then additional 57.3 RU from IL-23) from the two ligands binding to the bispecific antibody.

Inhibition of IL-23-Mediated Stat 3 Phosphorylation In Vitro from Kit225 Cells

Kit225 cells are a human T cell lymphocytic leukemia cell line that naturally expresses the IL-23 receptor. Incubation of Kit225 cells with human IL-23 results in the rapid increase of phosphorylation of Stat3 mediated by IL-23R/JAK kinase, which can be measured using commercially available ELISA.

Kit225 cells are routinely cultured in assay medium (RPMI 1640 containing 10% FBS, 10 ng/ml human IL-2, and 1× penicillin plus puromycin). On the day of assay, the cells are harvested, washed with large volume of serum free RPMI 1640 medium, then resuspended in serum free RPMI 1640 at $5 \times 10^6$ per ml. 500,000 Kit225 cells per well (in 100 µL) are added to the wells of a U-bottom cultured 96 well plate. The 96 well plate is placed in an incubator and the cells are starved for 3 hours at 37° C.

A dose range of the exemplified bispecific antibody from 100 nM to 0.5 pM, with 1:3 dilutions, is evaluated (MW of bispecific antibody is 200 kDa). Each test concentration of exemplified bispecific antibody is pre-incubated with (2 ng/ml) recombinant human IL-23 for 30 minutes at 37° C. Assay medium is used for "medium alone" and "medium with 2 ng/ml IL-23" controls. An IL-23 neutralizing antibody (parental IL-23 antibody described in U.S. Pat. No. 7,872,102), targeting the p19 subunit of IL-23, is used as a positive control in the assay and tested at the same molar range as the bispecific antibody. Control antibodies are also pre-incubated with (2 ng/ml) recombinant human IL-23 for 30 minutes at 37° C. Following pre-incubation, antibody/IL-23 mixtures are transferred to Kit225 cells and incubated for 15 minutes at 37° C.

At the end of the assay, the plates are centrifuged (3000 rpm for 2 minutes at 4° C.) and the supernatant is then discarded. Lysis buffer (100 µL, containing phosphate/proteinase inhibitor) is added to the cells and then incubated on ice for 5 minutes. Following incubation, the cells are centrifuged (3000 rpm for 5 minutes at 4° C.). After centrifugation, 100 µL of supernatant is transferred to 96 well plates (pre-coated with anti-Stat 3 antibody) for overnight incubation (4° C.). On the day of measuring Stat 3 phosphorylation by ELISA, the 96 well plates are warmed at room temperature and ELISA to determine Stat 3 phosphorylation levels is carried out according to manufacturer instructions (Cell Signaling Inc., Cat#7146). Following ELISA reactions, the 96 well plates are read at 450 nm on a microplate reader (Molecular Devises SpectraMax 190). Results are expressed as the concentration where 50% of the IL-23-induced Stat 3 phosphorylation is inhibited ($IC_{50}$) by either bispecific antibody or the positive control and is calculated using a 4 parameter sigmoidal fit of the data (GraphPad Prism).

The results demonstrate that the exemplified bispecific antibody of the present invention inhibited human IL-23 induced Stat 3 phosphorylation in Kit225 cells in a concentration-dependent manner. The inhibition was comparable to that observed with the positive control IL-23p19 antibody (with an $IC_{50}$ for bispecific antibody of 158±26 pM versus 75±7 pM for the positive control IL-23p19 antibody (average $IC_{50}$±SEM from three independent experiments)). Negative control antibody did not inhibit Stat 3 phosphorylation in Kit225 cells at any concentration tested. The exemplified bispecific antibody of the present invention effectively neutralized IL-23.

Inhibition of Soluble TNFα-Induced Cytotoxicity in L929 Cells In Vitro

L929 cells are mouse fibrosarcoma cells that naturally express the TNF receptor. Incubation of L929 cells with human TNFα results in rapid cell death due to excessive formation of reactive oxygen intermediates. Cell death can be measured using MTT cytotoxicity assay, where mitochondrial succinate dehydrogenase in viable cells reduces tetrazolium salt into formazan product, which can be detected with a microplate reader (Molecular Devices SpectriMax 190).

A dose range from 20 nM to 10 pM is evaluated (MW of the bispecific antibody is 200 kDa). Each test concentration of exemplified bispecific antibody (100 µL) is added to wells containing 200 pg/mL recombinant human TNFα and 6.25 µg/mL actinomycin-D. Testing is carried out in duplicate wells per treatment. A TNFα antibody, Adalimumab with IgG1 isotype (parental TNFα antibody, see for example U.S. Pat. No. 6,090,382), is used as a positive control in the assay. A human IgG1 isotype control antibody is used as a negative control. Control antibodies are tested at the same molar dose range as exemplified bispecific antibody. Plates containing antibody mixtures are incubated for 60 minutes at room temperature.

L929 cells are routinely cultured in assay medium (1×DMEM Cellgro, 10% FBS, 1% Pen-Strep, 1% MEM essential amino acids, 1% L-glutamine, 1% sodium pyruvate). On the day of the assay, the cells are rinsed with 1×PBS (no $Ca^{++}$ or $Mg^{++}$) and detached from culture flasks with 0.25% trypsin+EDTA. The trypsin is inactivated with assay medium. L929 cells are centrifuged at 215×g for 5 minutes at RT. The cell pellet is resuspended in assay medium. Cell density is measured with a hemocytometer, and 10,000 L929 cells (in 100 µL) are added to 96-well plates and placed in a tissue culture incubator (37° C., 95% relative humidity, 5% $CO_2$) over night. The antibody/TNFα/actinomycin-D mixture is transferred to the 96 well plates with L929 adherent cells and incubated (37° C., 95% relative humidity, 5% $CO_2$) 18 hours. The assay medium is removed and the MTT substrate mixture is added to the wells (120 µL). The plates are placed at 37° C., 95% relative humidity, 5% $CO_2$, for 3 hours. The cell death is determined by reading the plates at 490 nm on a microplate reader (Molecular Devices SpectraMax 190). Results are expressed as the concentration where 50% of the TNFα induced response is inhibited ($IC_{50}$) (average of three independent experiments±SEM) by either the bispecific antibody or the positive control antibody, calculated using a 4 parameter sigmoidal fit of the data (GraphPad Prism).

The results demonstrate that the exemplified bispecific antibody of the present invention inhibited human TNFα-induced killing of L929 cells in a concentration-dependent manner with an $IC_{50}$ of 233±20 pM. This inhibition was comparable to that observed with the positive control antibody, Adalimumab ($IC_{50}$=250±24 pM), whereas the negative control antibody did not inhibit human TNFα. The exemplified bispecific of the present invention effectively neutralized human TNFα.

Inhibition of Membrane Bound Human TNFα-Induced Cytotoxicity in L929 Cells In Vitro In order to study the ability of the bispecific antibody to inhibit membrane bound TNFα, known cleavage sites of TNFα are inactivated using a set of mutations previously demonstrated to allow expression of bioactive TNFα on cell surface (Mueller et. al. 1999) in the absence of TNFα cleavage. The non-cleavable TNFα construct is stably transfected to Chinese hamster ovary (CHO) cells. These cells express membrane bound TNFα as shown by flow cytometry. Incubation of L929 cells with CHO cells expressing human non-cleavable bound TNFα results in rapid L929 cell death.

CHO cells expressing membrane bound human TNFα are routinely maintained in selection medium (AM2001 media, an internal CHO growth media without MSX, 8 mM glutamine, GS supplement, HT supplement with 500 μg/mL G418). On the day of the assay, the cells are counted, rinsed with 1×PBS (no $Ca^{++}$ or $Mg^{++}$), centrifuged at 215×g for 5 min and re-suspended at 50,000 cells/mL in L929 assay medium together with Actinomycin-D (6.25 μg/mL final concentration). 500 cells (in 10 μL) of cell suspension are added to each concentration of antibody mixtures that were incubated for 60 minutes at 37° C., 95% relative humidity, 5% $CO_2$. The mixtures containing antibody, membrane bound human TNFα CHO cells, actinomycin-D mixtures are transferred to 96 well plates with L929 adherent cells and incubated 18 hours at 37° C., 95% relative humidity, 5% $CO_2$. The cell death is measured using an MTT cytotoxicity assay as described above for soluble TNFα L929 assay. Results are expressed as the concentration where 50% of the TNFα induced response is inhibited ($IC_{50}$) (average of 3 independent experiments±SEM) by either the bispecific or the positive control antibody.

The results demonstrate that the exemplified bispecific antibody of the present invention inhibited killing of L929 cells by human non-cleavable membrane bound TNFα CHO cells in a concentration-dependent manner with an $IC_{50}$ of 755±297 pM. This inhibition was comparable to that observed with the positive control antibody (Adalimumab with IgG1 isotype, $IC_{50}$=581±201 pM), whereas the negative control antibody did not inhibit human TNFα. The exemplified bispecific antibody of the present invention effectively neutralized membrane bound human TNFα.

Inhibition of Human IL-23-Induced mIL-22 Production In Vivo

Administration of human IL-23 induces expression of mouse IL-22 (mIL-22) in normal Balb C mice in vivo. This human IL-23-induced expression of mIL-22, in vivo, is blocked by the bispecific antibody of the present invention (which does not cross react with either mouse IL-23 or mouse TNFα).

Normal Balb C mice (N=8) are injected intraperitoneally with either 50 nmole/kg of exemplified bispecific antibody (molecular weight 200 kDa) or with a negative control antibody (human IgG1 isotype antibody, 50 nmole/kg, molecular weight 150 kDa). Three days following injection, the mice are challenged by intraperitoneal injection of 50 nmol/kg of human IL-23. Five hours post IL-23 challenge the mice are sacrificed and plasma is collected. Collected plasma is analyzed by commercial ELISA (eBioscience, Cat.#88-7422-86), according to manufacturer's instructions, for mouse IL-22 expression.

TABLE 5

Inhibition of human IL-23-induced mIL-22 production in vivo (relative to negative control antibody).

| | Bispecific Antibody + IL-23 | Naïve mouse | Negative Control Antibody (human IgG1 isotype antibody) + IL-23 |
|---|---|---|---|
| mIL22 Level (pg/mL) | 1.3 ± 2.6 | 0 ± 0 | 132 ± 51 |

The results demonstrate that the exemplified bispecific antibody of the present invention blocks the human IL-23-induced increase in mIL-22 expression. This inhibition is comparable to mouse IL-22 levels observed in naïve mice (p<0.0001, ANOVA followed by Turkey's Multiple Comparison test), whereas the negative control antibody did not inhibit the human IL-23-induced increase in expression of mIL-22. The bispecific antibody of the present invention effectively neutralized human IL-23.

Inhibition of Human TNFα-Induced Production of CXCL1 In Vivo

Administration of human TNFα induces a rapid and transient increase of mouse CXCL1 levels in plasma in regular Balb C mice, in vivo. This human TNFα-induced increase of mouse CXCL1 levels, in vivo, is blocked by the exemplified bispecific antibody of the present invention (which does not cross react with either mouse IL-23 or mouse TNFα).

Regular Balb C mice (N=8) are injected intraperitoneally with either: (a) 18 nmole/kg of bispecific antibody; (b) 18 nmole/kg of positive control anti-TNFα antibody (Adalimumab with IgG1 isotype); or (c) 18 nmole/kg of negative control antibody (human IgG1 isotype antibody). Three days following injection, the mice are challenged by intraperitoneal injection of 18 nmol/kg of human TNFα. Two hours post TNFα challenge the mice are sacrificed and plasma is collected. Collected plasma is analyzed by commercial MSD assay (Masol Scale Discovery, Cat.# K152QTG-1), according to manufacturer's instructions, for mouse CXCL1 levels.

TABLE 6

Inhibition of human TNFα-induced CXCL1 production in vivo (relative to negative control antibody).

| | Bispecific Antibody + TNFα | Positive Control Antibody (anti-TNFα antibody) + TNFα | Negative Control Antibody (human IgG1 isotype antibody) + TNFα | Naïve mouse |
|---|---|---|---|---|
| CXCL1 Level (pg/mL) | 622 ± 147 | 633 ± 162 | 2420 ± 850 | 16 ± 4.4 |

The results demonstrate that the exemplified bispecific antibody of the present invention significantly inhibited human TNFα-induced CXCL1 production relative to animals that received the negative control antibody (p<0.0001, ANOVA followed by Turkey's Multiple Comparison test). The reduction in CXCL1 production with the bispecific antibody was comparable to that observed with the positive control antibody. Thus, the exemplified bispecific antibody of the present invention effectively neutralized biological effects induced by human TNFα in mouse.

Comparison of Antibody Clearance with Parental IL-23 Antibody

In order to compare serum pharmacokinetics of the bispecific antibody with the serum pharmacokinetics of the parental IL-23 antibody (IL-23 antibody described in U.S. Pat. No. 7,872,102), male Cynomolgus monkeys are administered either the 5 mg/kg of exemplified bispecific antibody (intravenous (N=2); or subcutaneous (N=2)) or 5 mg/kg parental IL-23 antibody (intravenous (N=3)). Exemplified bispecific antibody is prepared in solution of 10 mM citrate (pH 6.0), 150 mM NaCl, 0.02% Tween 80. Parental IL-23 antibody is prepared in solution of phosphate-buffered saline (pH ~7.4).

Prior to administration, approximately 1.5 mL of blood is collected from each Cynomolgus monkey. Post administration, blood (approximately 1.5 mL) is collected at 1 (intravenous only), 6, 12, 24, 48, 72, 96, 168, 240, 336, 432, 504, 600 and 672 hours post administration. Blood samples are collected intravenously from a femoral vein into tubes serum separator tubes (e.g., containing no anticoagulant) and processed to serum.

Serum samples are analyzed by total human IgG ELISA utilizing AffiniPure F(ab')$_2$ Fragment Goat Anti-Human IgG (Jackson ImmunoResearch Laboratories, Inc.) as capture reagent coated on ELISA plates (Thermo Scientific™ Immulon® 4HBX). Serum samples (100 μL) are added to the individual wells of ELISA plate and incubated at 25° C. for 60 mins. Following incubation, 100 μL (10,000 fold dilution) mouse anti-human IgG Fc-HRP (Southern Biotech) is added to wells of ELISA plate for detection of exemplified bispecific antibody and 100 μL (10,000 fold dilution) mouse anti-human IgG$_4$ Fc-HRP (Southern Biotech) is added to wells of ELISA plate for detection of parental IL-23 antibody. Unbound enzyme is removed via washing and 100 μL TMB Microwell Peroxidase Substrate System (KPL) is added to individual wells of ELISA plate. Color development is stopped by addition of 100 μL TMB Stop Solution (KPL) and optical density of the wells is measured at 450 nm with wavelength correction set to 630 nm.

Standard curves for both exemplified bispecific antibody and parental IL-23 antibody, respectively, are generated by dilution of known amounts of exemplified bispecific antibody and parental IL-23 antibody, respectively, into 100% Cynomolgus monkey serum (BioreclamationIVT), followed by 5-fold dilution in blocker casein in PBS (Thermo Scientific™ Pierce™). Standard curve range of parental IL-23 antibody is 1.95-125 ng/mL (with an upper and lower limit of quantification of 50 ng/mL and 5 ng/mL, respectively); standard curve range of exemplified bispecific antibody is 15.63-1000 ng/mL (with an upper and lower limit of quantification of 450 ng/mL and 50 ng/mL, respectively).

Pharmacokinetic parameters (clearance values) are calculated using immunoreactivity versus time profile from time zero (administration of antibody) to 168 post administration (exemplified bispecific antibody) or 672 hours post administration (parental IL-23 antibody) and are determined via non-compartmental analysis using Phoenix (WinNonLin 6.3, Connect 1.3). Results are summarized in Table 8.

TABLE 8

Antibody clearance of exemplified bispecific antibody and parental IL-23 antibody in Cynomolgus monkey following single IV or subcutaneous administration.

| Antibody Administered | IV Clearance (mL/hr/kg) | Subcutaneous Clearance (mL/hr/kg) |
|---|---|---|
| Exemplified bispecific Ab | 0.23 | 0.34 |
| Parental IL-23 Ab | 1.17 ± 0.06 | N.A. |

The results demonstrate that the exemplified bispecific antibody has approximately 5-fold reduced antibody clearance compared to parental IL-23 antibody in Cynomolgus monkey.

Dual Neutralization of Murine IL-23 and Murine TNFα in an Anti-CD40 Antibody-Induced Murine Colitis Model The bispecific antibody of the present invention does not bind murine IL-23 (mIL23) or murine TNFα (mTNFα). Therefore, in order to test therapeutic potential of dual targeting TNFα and IL-23 in a rodent model, a surrogate bispecific antibody (surrogate bispecific) is generated. The surrogate bispecific is constructed of an engineered chimeric anti-TNFα mIgG2a antibody (engineered chimeric surrogate antibody of Adalimumab targeting equivalent mTNFα epitope, in mouse, as IgG of the bispecific antibody of the present invention targets in human), having fused at the C-terminus of both heavy chains of the anti-TNFα IgG2a antibody an engineered anti-IL-23p19 scFv (engineered from a surrogate murine antibody targeting an equivalent IL23p19 epitope, in mouse, as the scFv of the bispecific antibody of the present invention targets in human). The binding affinity to mIL23 and mTNFα of the surrogate bispecific is measured, using surface plasmon resonance, to be 1.51 nM and 0.08 nM, respectively.

The therapeutic potential of dual targeting TNFα and IL-23 for colitis is tested in an anti-CD40 antibody-induced murine colitis model by comparing the therapeutic effect (colon weight v. length) of the surrogate bispecific to the therapeutic effect of an anti-TNFα single antibody alone and an anti-IL-23 single antibody alone. Rag1 knockout mice, upon injection of murine anti-CD40 antibody, develop severe, acute colitis which leads to wasting disease, gastrointestinal symptoms including diarrhea and anal inflammation, and weight loss up to 10-20% within 4 days post injection.

To determine the therapeutic potential of dual targeting TNFα and IL-23, three days prior to injection of anti-CD40 antibody, Rag1 knockout mice are administered one of: (a) surrogate bispecific (1.4 mg/kg); (b) anti-TNFα antibody (1 mg/kg); (c) anti-IL-23 antibody (0.3 mg/kg); or (d) control IgG2a antibody (1 mg/kg) (these doses of antibody injection result in similar level of antibody exposure in vivo). Three days following injection, the mice are administered 200 μg per mouse of murine anti-CD40 antibody. Four days after administration of anti-CD40 antibody, the mice are sacrificed and colon weight and length are measured (a ratio of colon weight to length is determined as a measure of colon inflammation greater than mice not administered anti-CD40 antibody).

TABLE 9

Change in ratio (colon weight:length).

|  | Surrogate bispecific Ab | Anti-IL-23 Ab | Anti-TNFα Ab | Murine IgG2a Ab |
|---|---|---|---|---|
| Change in colon weight:length (mg/mm) | 2.68 ± 0.09 | 3.27 ± 0.09 | 3.18 ± 0.09 | 4 ± 0.098 |

The results demonstrate that dual blocking of TNFα and IL-23 by the surrogate bispecific antibody is superior for inhibiting colitis as compared to anti-IL-23 antibody and anti-TNFα antibody therapies alone (p<0.0001 compared to anti-IL-23 antibody alone; p<0.0004 compared to anti-TNF antibody alone, ABOVA followed by comparisons with control using Dunett's method). The inhibition of colitis with the surrogate bispecific was comparable to that observed with the control mice (not administered anti-CD40 antibody). Thus, dual blocking of TNF and IL-23 by the surrogate bispecific effectively inhibits colitis in mouse.

Dual Neutralization of Murine IL-23 and Murine TNFα in a Murine GPI-Induced Rheumatoid Arthritis Model DBA/1 mice, upon administration of glucose-6-phosphate-isomerase (GPI), develop rheumatoid arthritis characterized by rapid swelling in the paws. GPI is a protein in the glycolytic pathway and autoantibodies against GPI have been demonstrated in both human rheumatoid arthritis patients as well as murine models. Therapies targeting the TNFα or Th17 pathway alone have demonstrated efficacy in reducing joint swelling in the murine model (Matsumoto 2008, Iwanami 2008).

To demonstrate efficacy of dual neutralization of murine IL-23 and murine TNFα (by surrogate bispecific antibody, described above) when administered in an early therapeutic mode, DBA/1 mice are injected with 400 µg recombinant human GPI and complete Freund's adjuvant (CFA)(1:1 v/v, 2 subcutaneous injection sites at the base of the tail). Eight days following administration of GPI, the mice are administered (by twice weekly intra-peritoneal injection) one of: (a) control murine IgG2a antibody (90 µg); (b) surrogate bispecific (4.2 µg)+control murine IgG2a antibody (87 µg); (c) surrogate bispecific (12.6 µg)+control murine IgG2a antibody (81 µg); or (d) surrogate bispecific (42 µg)+control murine IgG2a antibody (60 µg). Three weeks (day 21) following administration of GPI, the mice are euthanized.

Starting on the day of administration of GPI (day 0) and days 2, 4, 7, 8, 9, 10, 11, 12, 14, 16, 18, and 21 thereafter, each paw is scored for severity of joint swelling based on a 0-3 scoring system (0=normal; 1=erythema and slight swelling of major joint; 2=moderate to severe swelling of the major joint; and 3=severe swelling of entire paw). The clinical score represents the total score of all 4 paws (a maximum score being 12). The area under curve (AUC) is calculated by trapezoid method for clinical score over time from day 1 to day 21 (the end of study). Clinical score AUC data (shown in Table 10 as mean±SEM) are fitted with a one-way ANOVA model for treatment groups. Test p values of interested comparisons are derived from model based T-test.

TABLE 10

Clinical scores for GPI-induced arthritis mice treated with surrogate bispecific antibody (at various doses) or control antibody. (p < 0.05 from model based t-test)

|  | Control Ab only | Surrogate Bis. (4.2 µg) + Control Ab (87 µg) | Surrogate Bis. (12.6 µg) + Control Ab (81 µg) | Surrogate Bis. (42 µg) + Control Ab (60 µg) |
|---|---|---|---|---|
| Clinical Score AUC | 105.3 ± 8.4 | 72.8 ± 14.5 | 32.9 ± 10.4 | 33.6 ± 8.9 |

The results demonstrate that dual blocking of TNFα and IL-23 by surrogate bispecific antibody reduces joint swelling of rheumatoid arthritis in a concentration-dependent manner. On day 9 (the day after treatment initiation with one of the control antibody or surrogate bispecific) mean clinical scores of mice treated with surrogate bispecific Ab are lower than control antibody-treated mice. Maximal clinical scores are attenuated by surrogate bispecific in a dose dependent manner, with clinical score AUCs for all three doses of surrogate bispecific-treated mice significantly lower than control antibody-treated mice (surrogate bispecific concentrations of 12.6 µg and 42 µg achieve the greatest percentage of attenuation).

Comparison of Dual Neutralization of Murine IL-23 and Murine TNFα in a Murine GPI-Induced Rheumatoid Arthritis Model with Neutralization of Murine IL-23 Alone and Murine TNFα Alone In order to compare efficacy of dual neutralization of murine IL-23 and murine TNFα (by surrogate bispecific antibody) to single murine IL-23 and single murine TNFα treatments when administered in an early therapeutic mode, DBA/1 mice are injected with 400 µg recombinant human GPI and CFA (1:1 v/v, 2 subcutaneous injection sites at the base of the tail). Eight days following administration of GPI, the mice are administered (by twice weekly intra-peritoneal injection) one of: (a) control murine IgG2a antibody (30 µg); (b) murine anti-IL-23 antibody (30 µg, an engineered surrogate murine antibody targeting an equivalent IL23p19 epitope, in mouse, as the scFv of the bispecific antibody of the present invention); (c) murine anti-TNFα antibody (30 µg, an engineered chimeric surrogate antibody of Adalimumab targeting an equivalent mTNFα epitope, in mouse, as IgG of the bispecific antibody of the present invention targets in human); or (d) surrogate bispecific (42 µg, described above). Twelve days (day 12) following administration of GPI, the mice are euthanized.

Starting on the day of administration of GPI (day 0) and days 2, 4, 7, 8, 9, 10, 11 and 12 thereafter, each paw is scored for severity of joint swelling based on a 0-3 scoring system (0=normal; 1=erythema and slight swelling of major joint; 2=moderate to severe swelling of the major joint; and 3=severe swelling of entire paw). The clinical score represents the total score of all 4 paws (a maximum score being 12). The area under curve (AUC) is calculated by trapezoid method for clinical score over time from day 8 (immunization with an antibody) to day 12 (end of study). Clinical score AUC data (shown in Table 11 as mean±SEM) are fitted with a one-way ANOVA model for treatment groups. Test p values of interested comparisons are derived from model based T-test. Clinical scores for each individual mouse for days 8 through 12 are fitted with a repeated measurement model with the factors if treatment groups, measurement days and their interaction. Autoregression structure modeling is also applied (to account for correlation of the same animal repeatedly measured across days). Synergy for each is assessed by constructing contrasts on interaction for the Bliss test.

TABLE 11

Clinical scores for GPI-induced arthritis mice treated with surrogate bispecific antibody, murine anti-IL-23 Ab, murine anti-TNFα Ab, or control antibody. ($p < 0.05$ from model based t-test)

|  | Control mIgG2a Ab | anti-IL-23 Ab | anti-TNFα Ab | Surrogate bispecific |
|---|---|---|---|---|
| Clinical Score AUC | 19.7 ± 3.6 | 18.4 ± 2.1 | 19.6 ± 4.1 | 6.1 ± 3.2 |

The results demonstrate that dual blocking of TNFα and IL-23 by surrogate bispecific antibody is superior for reducing joint swelling of rheumatoid arthritis as compared to anti-IL-23 antibody and anti-TNFα antibody therapies alone. On day 9 (the day after treatment initiation with one of the surrogate bispecific, anti-IL-23 antibody, anti-TNFα antibody or control antibody) mean clinical scores of mice treated with surrogate bispecific are lower than other treatment groups. Thus, dual blocking of TNFα and IL-23, by the surrogate bispecific, effectively reduces joint swelling of rheumatoid arthritis in mouse.

Sequences

Exemplified First Encoded Polypeptide; IgG HC, L1, scFv HCVR2, L2, and scFv LCVR2
(SEQ ID NO: 1)

EVQLVESGGG LVQPGRSLRL SCAASGFTFD DYAMHWVRQA PGKGLEWVSA ITWNSGHIDY

ADSVEGRFTI SRDNAKNSLY LQMNSLRAED TAVYYCAKVS YLSTASSLDY WGQGTLVTVS

SASTKGPSVF PLAPSSKSTS GGTAALGCLV KDYFPEPVTV SWNSGALTSG VHTFPAVLQS

SGLYSLSSVV TVPSSSLGTQ TYICNVNHKP SNTKVDKKVE PKSCDKTHTC PPCPAPELLG

GPSVFLFPPK PKDTLMISRT PEVTCVVVDV SHEDPEVKFN WYVDGVEVHN AKTKPREEQY

NSTYRVVSVL TVLHQDWLNG KEYKCKVSNK ALPAPIEKTI SKAKGQPREP QVYTLPPSRD

ELTKNQVSLT CLVKGFYPSD IAVEWESNGQ PENNYKTTPP VLDSDGSFFL YSKLTVDKSR

WQQGNVFSCS VMHEALHNHY TQKSLSLSPG GGGSGGGGSG GGGSQVQLVQ SGAEVKKPGS

SVKVSCKASG YPFTRYVMHW VRQAPGQCLE WMGYINPYND GVNYNEKFKG RVTITADEST

STAYMELSSL RSEDTAVYYC ARNWDTGLWG QGTTVTVSSG GGGSGGGGSG GGGSGGGGSD

IQMTQSPSSL SASVGDRVTI TCKASDHIGK FLTWYQQKPG KAPKLLIYGA TSKLTGVPSR

FSGSGSGTDF TLTISSLQPE DFATYYCQQY WSTPFTFGCG TKVEIK

Exemplified Second Encoded Polypeptide; IgG LC
(SEQ ID NO: 2)

DIQMTQSPSS LSASVGDRVT ITCRASQGIR NYLAWYQQKP GKAPKLLIYA ASTLQSGVPS

RFSGSGSGTD FTLTISSLQP EDVATYYCQR YNRAPYTFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC

DNA Seq. Encoding Exemplified First Polypeptide
(SEQ ID NO: 3)

atggagacagacacactcctgctatgggtactgctgctctgggttccaggctccactggc gaggtgcagctggtggagtctgggggaggcttggtacagcctggaggtccctgagactc tcctgtgcagcctctggattcacctttgatgactatgccatgcactgggtccgccaggct ccagggaaggggctggagtgggtgtcagctattacttggaatagtggtcacatagactac gcagactccgtggagggccggttcaccatctccagagacaatgccaagaactccctgtat ctgcaaatgaacagcctgagagccgaggacacggccgtatattactgtgcgaaagtgagc tacctgagtactgcctccagcctggactactggggccaaggaaccctggtcaccgtctcc tcagcctccaccaagggcccatcggtcttccccgctagcaccctcctccaagagcacctct gggggcacagcggccctgggctgcctggtcaaggactacttccccgaaccggtgacggtg tcgtggaactcaggcgccctgaccagcggcgtgcacaccttcccggctgtcctacagtcc tcaggactctactccctcagcagcgtggtgaccgtgccctccagcagcttgggcacccag acctacatctgcaacgtgaatcacaagcccagcaacaccaaggtggacaagaaagttgag cccaaatcttgtgacaaaactcacacatgcccaccgtgcccagcacctgaactcctgggg

| Sequences |
| --- | ggaccgtcagtcttcctcttccccccaaaacccaaggacaccctcatgatctcccggacc cctgaggtcacatgcgtggtggtggacgtgagccacgaagaccctgaggtcaagttcaac tggtacgtggacggcgtggaggtgcataatgccaagacaaagccgcgggaggagcagtac aacagcacgtaccgtgtggtcagcgtcctcaccgtcctgcaccaggactggctgaatggc aaggagtacaagtgcaaggtctccaacaaagcccTcccagccccatcgagaaaaccatc tccaaagccaaagggcagccccgagaaccacaggtgtacaccctgcccccatcccgggac gagctgaccaagaaccaggtcagcctgacctgcctggtcaaaggcttctatcccagcgac atcgccgtggagtgggagagcaatgggcagccggagaacaactacaagaccacgcccccc gtgctggactccgacggctccttcttcctctatagcaagctcaccgtggacaagagcagg tggcagcaggggaacgtcttctcatgctccgtgatgcatgaggctctgcacaaccactac acgcagaagagcctctccctgtctccgggtggcggaggctccgggggagggggtagcgga ggaggggatcccaggtgcagctggtgcagtctggggctgaggtgaagaagcctgggtcc tcggtgaaggtctcctgcaaggcttctggatatccattcactcgctatgttatgcactgg gtgcgacaggcccctggacaatgccttgagtggatgggatatattaatccttacaatgat ggtgtgaactacaatgagaagttcaaaggcagagtcacgattaccgcggacgaatccacg agcacagcctacatggagctgagcagcctgagatctgaggacacggccgtgtattactgt gcgagaaactgggacacaggcctctggggcaagggaccacggtcaccgtctcctcaggc ggcggaggctctggcggaggtggtagtggtggcggtggatcaggggggaggcggatctgac atccagatgacccagtctccatcctccctgtctgcatctgtaggagacagagtcaccatc acttgcaaggcaagtgaccacattggcaaattttTaacttggtatcagcagaaaccaggg aaagcccctaagctcctgatctatggtgcaaccagcaagctgactggggtcccatcaagg ttcagtggcagtggatctgggacagatttcactctcaccatcagcagtctgcaacctgaa gattttgcaacttactactgtcaacagtattggagtactccgttcacgttcggatgcggg accaaggtggaaataaaa DNA Seq. Encoding Exemplified Second Polypeptide (SEQ ID NO: 4)

atggagacagacacactcctgctatgggtactgctgctctgggttccaggatccactggc gacatccagatgacccagtctccatcctccctgtctgcatctgtaggagacagagtcacc atcacttgccgggcgagtcagggcattcgcaattatttagcctggtatcagcagaaacca gggaaagctcctaagctcctgatctatgctgcatccactttgcaatcaggggtcccatct cggttcagtggcagtggatctgggacagatttcactctcaccatcagcagcctgcagcct gaagatgttgcaacttattactgtcaacgctataaccgtgccccttacacgttcggccaa gggaccaaggtggaaatcaaacggactgtggctgcaccatctgtcttcatcttcccgcca tctgatgagcagttgaaatctggaactgcctctgttgtgtgcctgctgaataacttctat cccagagaggccaaagtacagtggaaggtggataacgccctccaatcgggtaactcccag gagagtgtcacagagcaggacagcaaggacagcacctacagcctcagcagcaccctgacg ctgagcaaagcagactacgagaaacacaaagtctacgcctgcgaagtcacccatcagggc ctgagctcgcccgtcacaaagagcttcaacaggggagagtgc

| Sequences |
|---|

Exemplified IgG Heavy Chain Variable Region 1
(SEQ ID NO: 5)
EVQLVESGGG LVQPGRSLRL SCAASGFTFD DYAMHWVRQA PGKGLEWVSA

ITWNSGHIDY ADSVEGRFTI SRDNAKNSLY LQMNSLRAED TAVYYCAKVS

YLSTASSLDY WGQGTLVTVS S

Exemplified scFv Heavy Chain Variable Region 2
(SEQ ID NO: 6)
QVQLVQ SGAEVKKPGS SVKVSCKASG YPFTRYVMHW VRQAPGQCLE

WMGYINPYND GVNYNEKFKG RVTITADEST STAYMELSSL RSEDTAVYYC

ARNWDTGLWG QGTTVTVSS

Exemplified IgG Light Chain Variable Region 1
(SEQ ID NO: 7)
DIQMTQSPSS LSASVGDRVT ITCRASQGIR NYLAWYQQKP GKAPKLLIYA ASTLQSGVPS

RFSGSGSGTD FTLTISSLQP EDVATYYCQR YNRAPYTFGQ GTKVEIK

Exemplified scFv Light Chain Variable Region 2
(SEQ ID NO: 8)
DIQMTQSPSSL SASVGDRVTI TCKASDHIGK FLTWYQQKPG KAPKLLIYGA

TSKLTGVPSR FSGSGSGTDF TLTISSLQPE DFATYYCQQY WSTPFTFGCG

TKVEIK

Exemplified HCDR1
(SEQ ID NO: 9)
AASGFTFDDYAMH

Exemplified HCDR2
(SEQ ID NO: 10)
AITWNSGHIDYADSVEG

Exemplified HCDR3
(SEQ ID NO: 11)
AKVSYLSTASSLDY

Exemplified HCDR4
(SEQ ID NO: 12)
KASGYPFTRYVMH

Exemplified HCDR5
(SEQ ID NO: 13)
YINPYNDGVNYNEKFKG

Exemplified HCDR6
(SEQ ID NO: 14)
ARNWDTGL

Exemplified LCDR1
(SEQ ID NO: 15)
RASQGIRNYLA

Exemplified LCDR2
(SEQ ID NO: 16)
YAASTLQS

Exemplified LCDR3
(SEQ ID NO: 17)
QRYNRAPYT

Exemplified LCDR4
(SEQ ID NO: 18)
KASDHIGKFLT

Exemplified LCDR5
(SEQ ID NO: 19)
YGATSKLT

| Sequences |
|---|
| Exemplified LCDR6 (SEQ ID NO: 20)<br>QQYWSTPFT<br><br>Exemplified Polypeptide Linker 1 (SEQ ID NO: 21)<br>GGGGSGGGGSGGGGS<br><br>Exemplified Polypeptide Linker 2 (SEQ ID NO: 22)<br>GGGGSGGGGSGGGGSGGGGS<br><br>Exemplified IgG Heavy Chain (SEQ ID NO: 23)<br>EVQLVESGGGLVQPGRSLRLSCAASGFTFDDYAMHWVRQAPGKGLEWVSAITWNSGHIDY<br>ADSVEGRFTISRDNAKNSLYLQMNSLRAEDTAVYYCAKVSYLSTASSLDYWGQGTLVTVS<br>SASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDKTHTCPPCPAPELLG<br>GPSVFLFPPKPKDTLMISRTPEVTCVVVDVSHEDPEVKFNWYVDGVEVHNAKTKPREEQY<br>NSTYRVVSVLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYSKLTVDKSR<br>WQQGNVFSCSVMHEALHNHYTQKSLSLSP |

We claim:

1. A bispecific antibody comprising an immunoglobulin G antibody (IgG) that binds tumor necrosis factor alpha (TNFα) conjugated to two single chain variable fragments (scFv) that bind the p19 subunit of IL-23 (IL23p19) wherein, a.) said IgG comprises two heavy chains (HC) and two light chains (LC), each HC comprises a heavy chain variable region (HCVR1) comprising heavy chain CDRs (HCDR) 1-3 and each LC comprises a light chain variable region (LCVR1) comprising light chain CDRs (LCDR) 1-3, wherein the amino acid sequence of HCDR1 is SEQ ID NO:9, the amino acid sequence of HCDR2 is SEQ ID NO:10, the amino acid sequence of HCDR3 is SEQ ID NO:11, the amino acid sequence of LCDR1 is SEQ ID NO:15, the amino acid sequence of LCDR2 is SEQ ID NO:16, and the amino acid sequence of LCDR3 is SEQ ID NO:17; and b.) each scFv comprises a heavy chain variable region (HCVR2) and a light chain variable region (LCVR2), the HCVR2 comprising HCDRs 4-6 and the LCVR2 comprising LCDRs 4-6, wherein the amino acid sequence of HCDR4 is SEQ ID NO:12, the amino acid sequence of HCDR5 is SEQ ID NO:13, the amino acid sequence of HCDR6 is SEQ ID NO:14, the amino acid sequence of LCDR4 is SEQ ID NO:18, the amino acid sequence of LCDR5 is SEQ ID NO:19, and the amino acid sequence of LCDR6 is SEQ ID NO:20, wherein each scFv is independently conjugated to said IgG antibody via a polypeptide linker (L1) covalently attached to the C-terminus of each IgG HC and the N-terminus of HCVR2 of each scFv, and the HCVR2 of each scFv is covalently attached to the LCVR2 of the same scFv via a second polypeptide linker (L2) covalently attached to the C-terminus of the HCVR2 and the N-terminus of the LCVR2 of the same scFv.

2. The bispecific antibody of claim 1, wherein the amino acid sequence of HCVR1 of each HC is SEQ ID NO:5, the amino acid sequence of LCVR1 of each LC is SEQ ID NO:7, the amino acid sequence of HCVR2 of each scFv is SEQ ID NO:6, and the amino acid sequence of LCVR2 of each scFv is SEQ ID NO:8.

3. The bispecific antibody of claim 1, wherein the amino acid sequence of each HC is SEQ ID NO:23, the amino acid sequence of each LC is SEQ ID NO:2, the amino acid sequence of HCVR2 of each scFv is SEQ ID NO:6, the amino acid sequence of LCVR2 of each scFv is SEQ ID NO:8, the amino acid sequence of L1 is SEQ ID NO:21, and the amino acid sequence of L2 is SEQ ID NO:22.

4. A method of treating ulcerative colitis or rheumatoid arthritis comprising administering to a patient in need thereof a therapeutically effective amount of a bispecific antibody of claim 1.

5. The method of claim 4, wherein the amino acid sequence of each HC of the bispecific antibody is SEQ ID NO:23, the amino acid sequence of each LC of the bispecific antibody is SEQ ID NO:2, the amino acid sequence of HCVR2 of each scFv of the bispecific antibody is SEQ ID NO:6, the amino acid sequence of LCVR2 of each scFv of the bispecific antibody is SEQ ID NO:8, the amino acid sequence of L1 of the bispecific antibody is SEQ ID NO:21, and the amino acid sequence of L2 of the bispecific antibody is SEQ ID NO:22.

6. A pharmaceutical composition comprising a bispecific antibody of claim 1 and one or more pharmaceutically acceptable carriers, diluents, or excipients.

7. The pharmaceutical composition of claim 6, wherein the amino acid sequence of each HC of the bispecific antibody is SEQ ID NO:23, the amino acid sequence of each LC of the bispecific antibody is SEQ ID NO:2, the amino acid sequence of HCVR2 of each scFv of the bispecific antibody is SEQ ID NO:6, the amino acid sequence of LCVR2 of each scFv of the bispecific antibody is SEQ ID NO:8, the amino acid sequence of L1 of the bispecific antibody is SEQ ID NO:21, and the amino acid sequence of L2 of the bispecific antibody is SEQ ID NO:22.

8. A DNA molecule comprising a polynucleotide sequence encoding a polypeptide chain of a bispecific antibody, said polypeptide chain comprising one HC, one scFv, one polypeptide linker and one second polypeptide linker of the bispecific antibody wherein the amino acid sequence of the encoded polypeptide chain is SEQ ID NO:1.

9. The DNA molecule of claim 8 further comprising a polynucleotide sequence encoding a polypeptide chain of the bispecific antibody, said polypeptide chain comprising one LC, wherein the amino acid sequence of the encoded polypeptide chain is SEQ ID NO:2.

* * * * *

SEQUENCE LISTING

<160> NUMBER OF SEQ ID NOS: 23

<210> SEQ ID NO 1
<211> LENGTH: 706
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly Ser
    450                 455                 460

Gln Val Gln Leu Val Gln Ser Gly Ala Glu Val Lys Lys Pro Gly Ser
465                 470                 475                 480

Ser Val Lys Val Ser Cys Lys Ala Ser Gly Tyr Pro Phe Thr Arg Tyr
                485                 490                 495

Val Met His Trp Val Arg Gln Ala Pro Gly Gln Cys Leu Glu Trp Met
            500                 505                 510

Gly Tyr Ile Asn Pro Tyr Asn Asp Gly Val Asn Tyr Asn Glu Lys Phe
        515                 520                 525

Lys Gly Arg Val Thr Ile Thr Ala Asp Glu Ser Thr Ser Thr Ala Tyr
    530                 535                 540

Met Glu Leu Ser Ser Leu Arg Ser Glu Asp Thr Ala Val Tyr Tyr Cys
545                 550                 555                 560

Ala Arg Asn Trp Asp Thr Gly Leu Trp Gly Gln Gly Thr Thr Val Thr
                565                 570                 575
```

```
Val Ser Ser Gly Gly Gly Ser Gly Gly Gly Ser Gly Gly
            580                 585                 590

Gly Ser Gly Gly Gly Ser Asp Ile Gln Met Thr Gln Ser Pro Ser
            595                 600                 605

Ser Leu Ser Ala Ser Val Gly Asp Arg Val Thr Ile Thr Cys Lys Ala
            610                 615                 620

Ser Asp His Ile Gly Lys Phe Leu Thr Trp Tyr Gln Gln Lys Pro Gly
625                 630                 635                 640

Lys Ala Pro Lys Leu Leu Ile Tyr Gly Ala Thr Ser Lys Leu Thr Gly
                    645                 650                 655

Val Pro Ser Arg Phe Ser Gly Ser Gly Ser Gly Thr Asp Phe Thr Leu
                660                 665                 670

Thr Ile Ser Ser Leu Gln Pro Glu Asp Phe Ala Thr Tyr Tyr Cys Gln
                675                 680                 685

Gln Tyr Trp Ser Thr Pro Phe Thr Phe Gly Cys Gly Thr Lys Val Glu
        690                 695                 700

Ile Lys
705
```

```
<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 2178
<212> TYPE: DNA
<213> ORGANISM: Artificial Sequence
<220> FEATURE:
<223> OTHER INFORMATION: Synthetic Construct

<400> SEQUENCE: 3

| | | | | | |
|---|---|---|---|---|---|
| atggagacag | acacactcct | gctatgggta | ctgctgctct | gggttccagg | ctccactggc | 60 |
| gaggtgcagc | tggtggagtc | tgggggaggc | ttggtacagc | ctgggaggtc | cctgagactc | 120 |
| tcctgtgcag | cctctggatt | cacctttgat | gactatgcca | tgcactgggt | ccgccaggct | 180 |
| ccagggaagg | ggctggagtg | ggtgtcagct | attacttgga | atagtggtca | catagactac | 240 |
| gcagactccg | tggagggccg | gttcaccatc | tccagagaca | atgccaagaa | ctccctgtat | 300 |
| ctgcaaatga | acagcctgag | agccgaggac | acggccgtat | attactgtgc | gaaagtgagc | 360 |
| tacctgagta | ctgcctccag | cctggactac | tggggccaag | gaaccctggt | caccgtctcc | 420 |
| tcagcctcca | ccaagggccc | atcggtcttc | ccgctagcac | cctcctccaa | gagcacctct | 480 |
| gggggcacag | cggccctggg | ctgcctggtc | aaggactact | tccccgaacc | ggtgacggtg | 540 |
| tcgtggaact | caggcgccct | gaccagcggc | gtgcacacct | tcccggctgt | cctacagtcc | 600 |
| tcaggactct | actccctcag | cagcgtggtg | accgtgccct | ccagcagctt | gggcacccag | 660 |
| acctacatct | gcaacgtgaa | tcacaagccc | agcaacacca | aggtggacaa | gaaagttgag | 720 |
| cccaaatctt | gtgacaaaac | tcacacatgc | ccaccgtgcc | cagcacctga | actcctgggg | 780 |
| ggaccgtcag | tcttcctctt | ccccccaaaa | cccaaggaca | ccctcatgat | ctcccggacc | 840 |
| cctgaggtca | catgcgtggt | ggtggacgtg | agccacgaag | accctgaggt | caagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | cccccatcga | gaaaaccatc | 1080 |
| tccaaagcca | aagggcagcc | ccgagaacca | caggtgtaca | ccctgccccc | atcccgggac | 1140 |
| gagctgacca | agaaccaggt | cagcctgacc | tgcctggtca | aaggcttcta | tcccagcgac | 1200 |
| atcgccgtgg | agtgggagag | caatgggcag | ccggagaaca | actacaagac | cacgccccc | 1260 |
| gtgctggact | ccgacggctc | cttcttcctc | tatagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctccct | gtctccgggt | ggcggaggct | ccggggggag | gggtagcgga | 1440 |
| ggaggggggat | cccaggtgca | gctggtgcag | tctgggctg | aggtgaagaa | gcctgggtcc | 1500 |
| tcggtgaagg | tctcctgcaa | ggcttctgga | tatccattca | ctcgctatgt | tatgcactgg | 1560 |
| gtgcgacagg | cccctggaca | atggccttgag | tggatgggat | atattaatcc | ttacaatgat | 1620 |
| ggtgtgaact | acaatgagaa | gttcaaaggc | agagtcacga | ttaccgcgga | cgaatccacg | 1680 |
| agcacagcct | acatggagct | gagcagcctg | agatctgagg | acacggccgt | gtattactgt | 1740 |
| gcgagaaaact | gggacacagg | cctctggggg | caagggacca | cggtcaccgt | ctcctcaggc | 1800 |
| ggcgaggct | ctggcggagg | tggtagtggt | ggcggtggat | caggggggagg | cggatctgac | 1860 |
| atccagatga | cccagtctcc | atcctccctg | tctgcatctg | taggagacag | agtcaccatc | 1920 |
| acttgcaagg | caagtgacca | cattggcaaa | tttttaactt | ggtatcagca | gaaaccaggg | 1980 |
| aaagccccta | agctcctgat | ctatggtgca | accagcaagc | tgactggggt | cccatcaagg | 2040 |
| ttcagtggca | gtggatctgg | gacagatttc | actctcacca | tcagcagtct | gcaacctgaa | 2100 |

```
gattttgcaa cttactactg tcaacagtat tggagtactc cgttcacgtt cggatgcggg    2160
accaaggtgg aaataaaa                                                  2178

<210> SEQ ID NO 4
<211> LENGTH: 702
<212> TYPE: DNA
<213> ORGANISM: Artificial Sequence
<220> FEATURE:
<223> OTHER INFORMATION: Synthetic Construct

<400> SEQUENCE: 4
atggagacag acacactcct gctatgggta ctgctgctct gggttccagg atccactggc      60
gacatccaga tgacccagtc tccatcctcc ctgtctgcat ctgtaggaga cagagtcacc     120
atcacttgcc gggcgagtca gggcattcgc aattatttag cctggtatca gcagaaacca     180
gggaaagctc ctaagctcct gatctatgct gcatccactt gcaatcagg ggtcccatct      240 cggttcagtg gcagtggatc tgggacagat ttcactctca ccatcagcag cctgcagcct     300
gaagatgttg caacttatta ctgtcaacgc tataaccgtg ccccttacac gttcggccaa     360
gggaccaagg tggaaatcaa acggactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600 ctgagcaaag cagactacga gaaacacaaa gtctacgcct gcgaagtcac ccatcagggc     660
ctgagctcgc ccgtcacaaa gagcttcaac aggggagagt gc                        702

<210> SEQ ID NO 5
<211> LENGTH: 121
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 6
<211> LENGTH: 115
<212> TYPE: PRT
<213> ORGANISM: Artificial Sequence
<220> FEATURE:
```

<223> OTHER INFORMATION: Synthetic Construct

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Pro Phe Thr Arg Tyr
            20                  25                  30

Val Met His Trp Val Arg Gln Ala Pro Gly Gln Cys Leu Glu Trp Met
        35                  40                  45

Gly Tyr Ile Asn Pro Tyr Asn Asp Gly Val Asn Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Asp Thr Gly Leu Trp Gly Gln Gly Thr Thr Val Thr
            100                 105                 110

Val Ser Ser
        115

<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Gly Lys Phe
            20                  25                  30

Leu Thr Trp Tyr Gln Gln Lys Pro Gly Lys Ala Pro Lys Leu Leu Ile
        35                  40                  45

Tyr Gly Ala Thr Ser Lys Leu Thr Gly Val Pro Ser Arg Phe Ser Gly

```
            50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Ser Thr Pro Phe
                 85                  90                  95

Thr Phe Gly Cys Gly Thr Lys Val Glu Ile Lys
            100                 105
```

<210> SEQ ID NO 9
<211> LENGTH: 13
<212> TYPE: PRT
<213> ORGANISM: Artificial Sequence
<220> FEATURE:
<223> OTHER INFORMATION: Synthetic Construct

<400> SEQUENCE: 9

```
Ala Ala Ser Gly Phe Thr Phe Asp Asp Tyr Ala Met His
 1               5                  10
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

```
Ala Ile Thr Trp Asn Ser Gly His Ile Asp Tyr Ala Asp Ser Val Glu
 1               5                  10                  15

Gly
```

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

```
Ala Lys Val Ser Tyr Leu Ser Thr Ala Ser Ser Leu Asp Tyr
 1               5                  10
```

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

```
Lys Ala Ser Gly Tyr Pro Phe Thr Arg Tyr Val Met His
 1               5                  10
```

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

```
Tyr Ile Asn Pro Tyr Asn Asp Gly Val Asn Tyr Asn Glu Lys Phe Lys
 1               5                  10                  15

Gly
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ala Arg Asn Trp Asp Thr Gly Leu
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Arg Ala Ser Gln Gly Ile Arg Asn Tyr Leu Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Tyr Ala Ala Ser Thr Leu Gln Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Gln Arg Tyr Asn Arg Ala Pro Tyr Thr
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Lys Ala Ser Asp His Ile Gly Lys Phe Leu Thr
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Tyr Gly Ala Thr Ser Lys Leu Thr
1               5

-continued

```
<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Tyr Trp Ser Thr Pro Phe Thr
1               5

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Synthetic Construct

<400> SEQUENCE: 22

Gly Gly Gly Gly Ser Gly Gly Gly Gly Ser Gly Gly Gly Gly Ser Gly
1               5                   10                  15

Gly Gly Gly Ser
            20

<210> SEQ ID NO 23
<211> LENGTH: 449
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro
```